(12) United States Patent
Auerbach et al.

(10) Patent No.: US 12,165,324 B2
(45) Date of Patent: Dec. 10, 2024

(54) AUTOMATICALLY IDENTIFYING SCAR AREAS WITHIN ORGANIC TISSUE USING MULTIPLE IMAGING MODALITIES

(71) Applicant: Biosense Webster (Israel) Ltd., Yokneam (IL)

(72) Inventors: Shmuel Auerbach, Kerem Maharal (IL); Ana Kaufman, Zichron Yalakov (IL); Shiran Eliyahu, Yokneam Illit (IL)

(73) Assignee: BIOSENSE WEBSTER (ISRAEL) LTD., Yokneam (IL)

( * ) Notice: Subject to any disclaimer, the term of this patent is extended or adjusted under 35 U.S.C. 154(b) by 391 days.

(21) Appl. No.: 17/384,989

(22) Filed: Jul. 26, 2021

(65) Prior Publication Data
US 2022/0036555 A1  Feb. 3, 2022

Related U.S. Application Data

(60) Provisional application No. 63/058,439, filed on Jul. 29, 2020.

(51) Int. Cl.
*G06T 7/00* (2017.01)
*A61B 5/35* (2021.01)
(Continued)

(52) U.S. Cl.
CPC .............. *G06T 7/0016* (2013.01); *A61B 5/35* (2021.01); *A61B 5/361* (2021.01); *A61B 5/363* (2021.01);
(Continued)

(58) Field of Classification Search
CPC ......... G06T 7/0016; G06T 2207/10088; G06T 2207/10132; G06T 2207/20081;
(Continued)

(56) References Cited

U.S. PATENT DOCUMENTS

2016/0098833 A1* 4/2016 Tsadok ................. G06T 3/0093
382/128
2017/0217102 A1 8/2017 Mansi et al.
(Continued)

OTHER PUBLICATIONS

Extended European Search Report dated Dec. 23, 2021 for European Patent Application No. 21188396.2.
(Continued)

*Primary Examiner* — Michael R Neff
(74) *Attorney, Agent, or Firm* — VOLPE KOENIG

(57) ABSTRACT

A method and apparatus for implementing scar tissue identification using a processor coupled to a memory is disclosed. The method and apparatus receive a first modality and a second modality. The first modality is of a first type. The second modality is of a second type, which is different from the first type. Each of the first modality and the second modality respectively describe organic tissue of a patient according to the first and second types. The method and apparatus cross reference the first modality and the second modality and generates improved image data for the first modality based on the cross referencing. The image data includes enhanced accuracy over or higher resolution than original data of the first modality.

30 Claims, 11 Drawing Sheets

(51) Int. Cl.
  *A61B 5/361* (2021.01)
  *A61B 5/363* (2021.01)
  *A61B 5/367* (2021.01)

(52) U.S. Cl.
  CPC .... *A61B 5/367* (2021.01); *G06T 2207/10088* (2013.01); *G06T 2207/10132* (2013.01); *G06T 2207/20081* (2013.01); *G06T 2207/20084* (2013.01); *G06T 2207/30048* (2013.01)

(58) Field of Classification Search
  CPC . G06T 2207/20084; G06T 2207/30048; A61B 5/361; A61B 5/35; A61B 5/363; A61B 5/367
  USPC .......................................................... 382/128
  See application file for complete search history.

(56) References Cited

U.S. PATENT DOCUMENTS

| | | | |
|---|---|---|---|
| 2018/0033166 A1* | 2/2018 | Cachovan | G06T 11/006 |
| 2018/0249979 A1* | 9/2018 | Wang | A61B 5/055 |
| 2019/0139236 A1* | 5/2019 | Cheng | G16H 20/40 |
| 2020/0218922 A1* | 7/2020 | Chen | A61B 5/0022 |
| 2020/0297284 A1* | 9/2020 | O'Brien | G16H 50/20 |

OTHER PUBLICATIONS

Hatt, Charles R et al. "MRI-3D ultrasound-X-ray image fusion with electromagnetic tracking for transendocardial therapeutic injections: in-vitro validation and in-vivo feasibility." Computerized medical imaging and graphics : the official journal of the Computerized Medical Imaging Society vol. 37,2 (2013).

Bruge et al., "Multi-modal data fusion for Cardiac Resynchronization Therapy planning and assistance," 2015 37th Annual International Conference of the IEEE Engineering in Medicine and Biology Society (EMBC), pp. 2391-2394 (2015).

Tian, Jing et al. "Multimodality fusion imaging using delayed-enhanced cardiac magnetic resonance imaging, computed tomography, positron emission tomography, and real-time intracardiac echocardiography to guide ventricular tachycardia ablation in implantable cardioverter-defibrillator patients." Heart rhythm vol. 6,6 pp. 825-828 (2009).

Boveiri et al., "Medical image registration using deep neural networks: A comprehensive review", Computers & Electrical Engineering, Pergamon Press, GB, vol. 87, (2020).

Communication pursuant to Article 94(3) EPC dated Aug. 22, 2024 for European Patent Application No. 21 188 396.2.

* cited by examiner

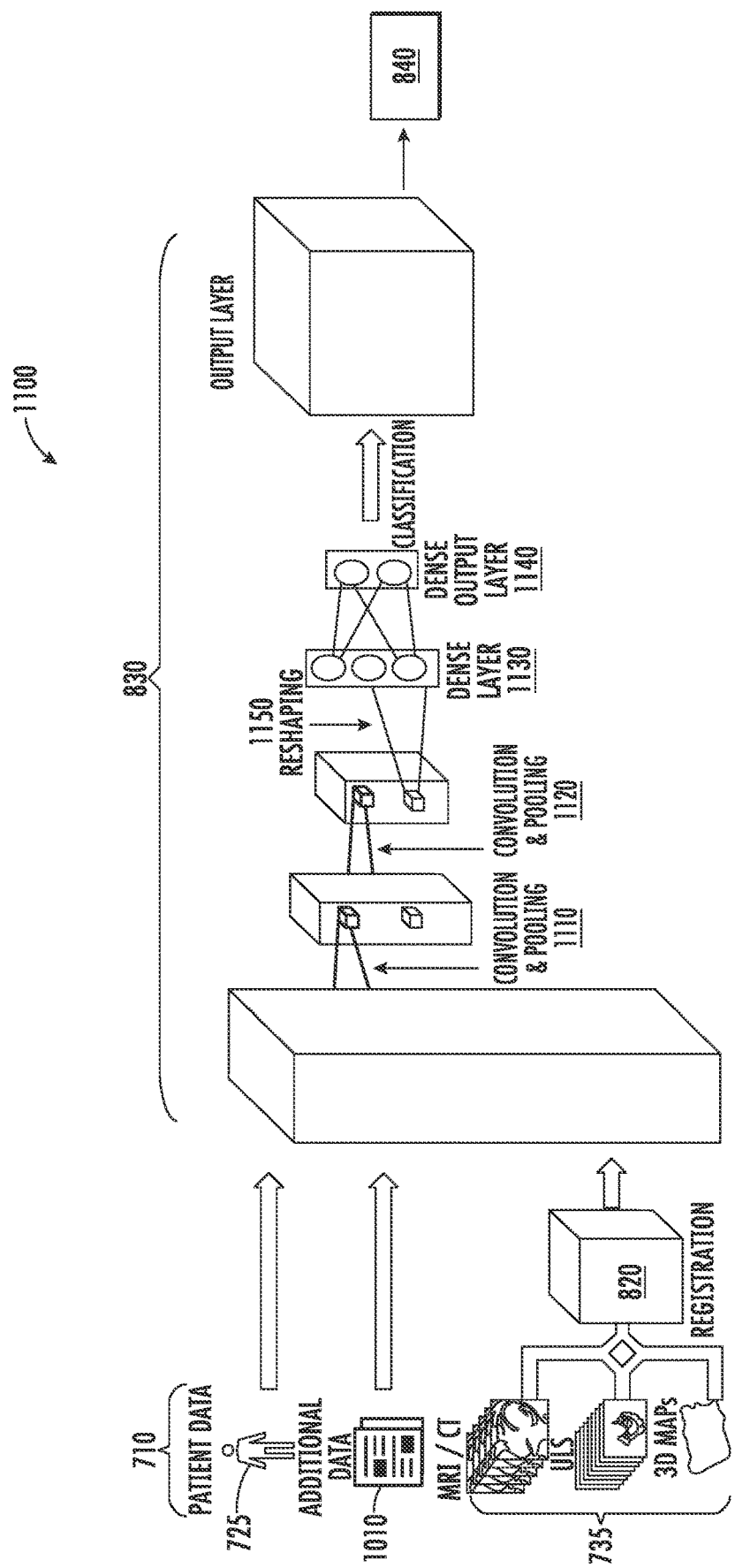

AUTOMATICALLY IDENTIFYING SCAR AREAS WITHIN ORGANIC TISSUE USING MULTIPLE IMAGING MODALITIES

CROSS REFERENCE TO RELATED APPLICATIONS

This application claims the benefit of U.S. Provisional Patent Application No. 63/058,439, filed Jul. 29, 2020, which is incorporated by reference as if fully set forth.

FIELD OF INVENTION

The present invention is related to an artificial intelligence and machine learning method and system. More particularly, the present invention relates to a system and method that automatically identifies scar areas within organic tissue based on multiple imaging modalities.

BACKGROUND

Treatments for cardiac conditions, such as cardiac arrhythmia, often require heart imaging (i.e., imaging cardiac tissue, chambers, veins, arteries and/or pathways, which is also known as cardiac scanning or cardiac imaging). With heart imaging, being able to identify scar tissue allows a characterization of cardiac substrates and understanding of arrhythmia mechanisms. Conventional imaging modalities, examples of which include ultrasound imaging and magnetic resonance imaging (MRI), can be used to identify scar tissue, but not without limitation. While ultrasound imaging is a readily available real-time tool, ultrasound imaging is operator dependent (thereby exposing results to a subjective interpretation) and has lower resolution compared to other conventional imaging modalities. MRI may utilize a late gadolinium enhancement (LGE) technology to output a higher resolution than ultrasound imaging; however, MRI does not have real-time availability, is relatively costly, and a resulting voltage mapping lacks an ability to evaluate an entire depth of cardiac tissue. Due to the limitations of conventional imaging modalities, a need exists to provide improved methods for heart imaging.

SUMMARY

According to an embodiment, a method and apparatus is provided for implementing a scar tissue identifier using a processor coupled to a memory. The method and apparatus receives a first modality and a second modality. The first modality is of a first type. The second modality is of a second type, which is different from the first type. Each of the first modality and the second modality respectively describe organic tissue of a patient according to the first and second types. The method and apparatus cross references the first modality and the second modality and generates improved image data for the first modality based on the cross referencing. The improved image data includes enhanced accuracy over or higher resolution than original data of the first modality.

According to one or more embodiments, the method embodiment above can be implemented within an apparatus, a system, and/or a computer program product.

BRIEF DESCRIPTION OF THE DRAWINGS

A more detailed understanding may be had from the following description, given by way of example in conjunction with the accompanying drawings, wherein like reference numerals in the figures indicate like elements, and wherein:

FIG. 11 illustrates a system using a neural network in accordance with the embodiments described herein.

DETAILED DESCRIPTION

Figure 1:
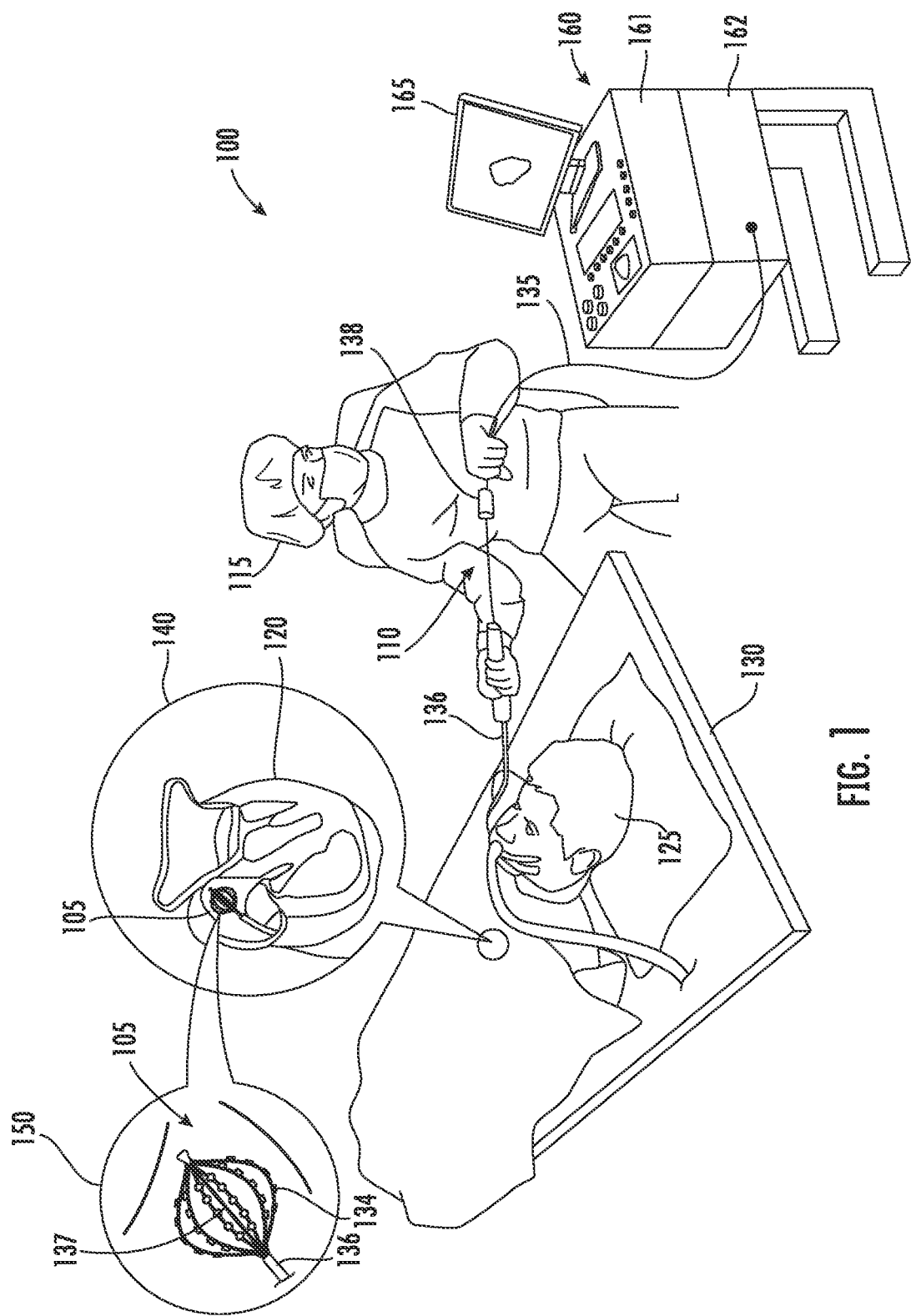
FIG. 1 illustrates a diagram of an exemplary system in which one or more features of the disclosure subject matter can be implemented.

Disclosed herein is an artificial intelligence and machine learning method and system. More particularly, this disclosure relates to a system and method that automatically identifies scar areas within organic tissue (e.g., a heart) based on multiple imaging modalities. The system and method include a processor executable code or software that is necessarily rooted in process operations by, and in processing hardware of, medical device equipment to improve one modality based on another modality. According to an embodiment, the system and method provide a specific multi-step data manipulation of the multiple imaging modalities that provides more accurate and higher resolution real-time image data than conventional imaging modalities in support of better diagnoses (e.g., as this real-time image data is not available via conventional imaging modalities). In this regard and in operation, the system and method cross reference different modalities to strengthen findings of a single modality.

For example, the system and method operating to identify scar tissue accesses or receives one or more images from an ultrasound (e.g., at least one of a first modality of a first/same type) and data from LGE-MRI (e.g., a second modality of a second/different type) of organic tissue of a patient (e.g., a heart). The system and method operating to identify scar tissue, then, cross references these ultrasound images to the LGE-MRI data by comparing and matching locations of each of the ultrasound images to corresponding locations on the LGE-MRI data (e.g., based on a voltage). In this way, the system and method operating to identify scar tissue utilizes imaging processing (and/or other methods) to implement the cross referencing and to adjust and interpret data of the ultrasound images based on the LGE-MRI data. The data of the ultrasound images after adjustment and interpretation is used by the system and method operating to identify scar tissue to automatically identify scar areas within the organic tissue.

The technical effects and benefits of the system and method operating to identify scar tissue include generating more accurate and higher resolution real-time image data for the ultrasound images (e.g., enhanced accuracy over or higher resolution than original data of the first modality) without relying on a human operator's subjective interpretation (as in conventional imaging modalities). The system and method operating to identify scar tissue and the generated real-time image data also enables an evaluation of the entire depth of the organic tissue, overcomes the lower resolution of conventional ultrasound imaging, and is relatively inexpensive and available compared to MRIs. The system and method operating to identify scar tissue may be practically applied, but not limited to, ablation-ultrasound technologies, planning and diagnosis of lesions, and assessment and diagnosis of magnetic resonance to address one or more disease states, such as atrial fibrillation, atrial flutter, general electrophysiology, arrhythmias, ventricular fibrillation, and ventricular tachycardia.

FIG. 1 is a diagram of an exemplary system 100 (e.g., medical device equipment) in which one or more features of the disclosure subject matter can be implemented. All or parts of system 100 may be used to collect information for an imaging dataset (e.g., a training dataset) and/or all or parts of system 100 may be used to implement the scar tissue identifier described herein.

The system 100 may include components, such as a catheter 105, that are configured to use intravascular ultrasound and/or MRI catheterization to image of an intra-body organ. The catheter 105 may also be further configured to obtain biometric data including the electrical signals of the heart (e.g., the intracardiac signals). Although the catheter 105 is shown to be a point catheter, it will be understood that a catheter of any shape that includes one or more elements (e.g., electrodes, tracking coils, piezoelectric transducer, etc.) may be used to implement the embodiments disclosed herein.

The system 100 includes a probe 110, having shafts that may be navigated by a physician or a medical professional 115 into a body part, such as a heart 120, of a patient 125 lying on a bed (or a table) 130. According to embodiments, multiple probes may be provided; however, for purposes of conciseness, a single probe 110 is described herein. Yet, it is understood that the probe 110 may represent multiple probes.

The exemplary system 100 can be utilized to detect, diagnose, and treat cardiac conditions (e.g., using the scar tissue identifier). Cardiac conditions, such as cardiac arrhythmias (atrial fibrillation in particular), persist as common and dangerous medical ailments, especially in the aging population. In patients (e.g., the patient 125) with normal sinus rhythm, the heart (e.g., the heart 120), which includes atrial, ventricular, and excitatory conduction tissue, is electrically excited to beat in a synchronous, patterned fashion (note that this electrical excitement can be detected as intracardiac signals or the like).

In patients (e.g., the patient 125) with cardiac arrhythmias, abnormal regions of cardiac tissue do not follow the synchronous beating cycle associated with normally conductive tissue as in patients with normal sinus rhythm. Instead, the abnormal regions of cardiac tissue aberrantly conduct to adjacent tissue, thereby disrupting the cardiac cycle into an asynchronous cardiac rhythm (note that this asynchronous cardiac rhythm can also be detected as intracardiac signals). Such abnormal conduction has been previously known to occur at various regions of the heart (e.g., the heart 120), for example, in the region of the sino-atrial (SA) node, along the conduction pathways of the atrioventricular (AV) node, or in the cardiac muscle tissue forming the walls of the ventricular and atrial cardiac chambers.

Further, cardiac arrhythmias, including atrial arrhythmias, may be of a multiwavelet reentrant type, characterized by multiple asynchronous loops of electrical impulses that are scattered about the atrial chamber and are often self-propagating (e.g., another example of intracardiac signals). Alternatively, or in addition to the multiwavelet reentrant type, cardiac arrhythmias may also have a focal origin, such as when an isolated region of tissue in an atrium fires autonomously in a rapid, repetitive fashion (e.g., another example of the intracardiac signals). Ventricular tachycardia (V-tach or VT) is a tachycardia, or fast heart rhythm that originates in one of the ventricles of the heart. This is a potentially life-threatening arrhythmia because it may lead to ventricular fibrillation and sudden death.

One type of arrhythmia, atrial fibrillation, occurs when the normal electrical impulses (e.g., another example of the intracardiac signals) generated by the sinoatrial node are overwhelmed by disorganized electrical impulses (e.g., the signal interference) that originate in the atria and pulmonary veins causing irregular impulses to be conducted to the ventricles. An irregular heartbeat results and may last from minutes to weeks, or even years. Atrial fibrillation (AF) is often a chronic condition that leads to a small increase in the risk of death often due to strokes. The first line of treatment for AF is medication that either slows the heart rate or revert the heart rhythm back to normal. Additionally, persons with AF are often given anticoagulants to protect them from the risk of stroke. The use of such anticoagulants comes with its own risk of internal bleeding. In some patients, medication is not sufficient and their AF is deemed to be drug-refractory, i.e., untreatable with standard pharmacological interventions. Synchronized electrical cardioversion may also be used to convert AF to a normal heart rhythm. Alternatively, AF patients are treated by catheter ablation.

A catheter ablation-based treatment may include mapping the electrical properties of heart tissue, especially the endocardium and the heart volume, and selectively ablating cardiac tissue by application of energy. Cardiac mapping (which is an example of heart imaging) includes creating a map of electrical potentials (e.g., a voltage map) of the wave propagation along the heart tissue or a map of arrival times (e.g., a local time activation (LAT) map) to various tissue located points. Cardiac mapping (e.g., a cardiac map) may be used for detecting local heart tissue dysfunction. Ablations, such as those based on cardiac mapping, can cease or modify the propagation of unwanted electrical signals from one portion of the heart to another, thus restoring normal sinus rhythm.

The ablation process damages the unwanted electrical pathways by formation of non-conducting lesions. Various energy delivery modalities have been disclosed for forming lesions, and include use of microwave, laser, cryoablation and more commonly, radiofrequency energies to create conduction blocks along the cardiac tissue wall. In a two-step procedure—mapping followed by ablation—electrical activity at points within the heart is typically sensed and measured by advancing a catheter (e.g., the catheter 105) containing one or more electrical sensors (e.g., the at least one ablation electrode 134 of the catheter 105) into the heart (e.g., the heart 120), and acquiring data at a multiplicity of points. This data (e.g., biometric data including the intracardiac signals and 3D locations) is then utilized to identify the endocardial target areas, at which ablation is to be performed. Note that, due to the use of the scar tissue identifier employed by the exemplary system 100 (e.g., medical device equipment), more accurate and higher resolution real-time image data is provided to support of better diagnoses.

Cardiac ablation and other cardiac electrophysiological procedures have become increasingly complex as clinicians treat challenging conditions such as atrial fibrillation and ventricular tachycardia. The treatment of complex arrhythmias can now rely on the use of three-dimensional (3D) mapping systems in order to reconstruct the anatomy of the heart chamber of interest. In this regard, the scar tissue identifier employed by the exemplary system 100 (e.g., medical device equipment) herein provides the underlying real-time image data so that improved images, scans, and/or maps for treating cardiac conditions can be generated.

For example, cardiologists rely upon software, such as the Complex Fractionated Atrial Electrograms (CFAE) module of the CARTO® 3 3D mapping system, produced by Biosense Webster, Inc. (Irvine, Calif.), to generate and analyze intracardiac electrograms (EGM). The scar tissue identifier of the exemplary system 100 (e.g., medical device equipment) enhances this software to generate and analyze improved intracardiac images, scans, and/or maps so that the ablation points can be determined for treatment of a broad range of cardiac conditions, including atypical atrial flutter and ventricular tachycardia.

The improved images, scans, and/or maps supported by the scar tissue identifier can provide multiple pieces of information regarding the electrophysiological properties of the intra-body organ (e.g., heart and/or organic tissue including the scar tissue) that represent the cardiac substrates (anatomical and functional) of these challenging arrhythmias.

Cardiomyopathies with different etiologies (ischemic, dilated cardiomyopathy (DCM), hypertrophic cardiomyopathy (HCM), arrhythmogenic right ventricular dysplasia (ARVD), left ventricular non-compaction (LVNC), etc.) have an identifiable substrate, featured by areas of unhealthy tissue surrounded by areas of normally functioning cardiomyocytes.

Abnormal tissue is generally characterized by low-voltage EGMs. However, initial clinical experience in endo-epicardial mapping indicates that areas of low-voltage are not always present as the sole arrhythmogenic mechanism in such patients. In fact, areas of low or medium voltage may exhibit EGM fragmentation and prolonged activities during sinus rhythm, which corresponds to the critical isthmus identified during sustained and organized ventricular arrhythmias, e.g., applies only to non-tolerated ventricular tachycardias. Moreover, in many cases, EGM fragmentation and prolonged activities are observed in the regions showing a normal or near-normal voltage amplitude (>1-0.5 mV). Although the latter areas may be evaluated according to the voltage amplitude, they cannot be considered as normal according to the intracardiac signal, thus representing a true arrhythmogenic substrate. The 3D mapping may be able to localize the arrhythmogenic substrate on the endocardial and/or epicardial layer of the right/left ventricle, which may vary in distribution according to the extension of the main disease.

The substrate linked to these cardiac conditions is related to the presence of fragmented and prolonged EGMs in the endocardial and/or epicardial layers of the ventricular chambers (right and left). The 3D mapping system, such as CARTO® 3, is able to localize the potential arrhythmogenic substrate of the cardiomyopathy in terms of abnormal EGM detection.

Electrode catheters (e.g., the catheter 105) are use in medical practice. Electrode catheters are used to stimulate and map electrical activity in the heart and to ablate sites of aberrant electrical activity. In use, the electrode catheter is inserted into a major vein or artery, e.g., femoral artery, and then guided into the chamber of the heart. A typical ablation procedure involves the insertion of a catheter having at least one electrode at its distal end, into a heart chamber. A reference electrode is provided, generally taped to the skin of the patient or by means of a second catheter that is positioned in or near the heart. Radio frequency (RF) current is applied to the tip electrode of the ablating catheter, and current flows through the media that surrounds it, i.e., blood and tissue, toward the reference electrode. The distribution of current depends on the amount of electrode surface in contact with the tissue as compared to blood, which has a higher conductivity than the tissue. Heating of the tissue occurs due to its electrical resistance. The tissue is heated sufficiently to cause cellular destruction in the cardiac tissue resulting in formation of a lesion within the cardiac tissue which is electrically non-conductive. During this process, heating of the electrode also occurs as a result of conduction from the heated tissue to the electrode itself. If the electrode temperature becomes sufficiently high, possibly above 60 degrees Celsius, a thin transparent coating of dehydrated blood protein can form on the surface of the electrode. If the temperature continues to rise, this dehydrated layer can become progressively thicker resulting in blood coagulation on the electrode surface. Because dehydrated biological material has a higher electrical resistance than endocardial tissue, impedance to the flow of electrical energy into the tissue also increases. If the impedance increases sufficiently, an impedance rise occurs, and the catheter must be removed from the body and the tip electrode cleaned.

Treatments for cardiac conditions such as cardiac arrhythmia often require obtaining a detailed mapping of cardiac tissue, chambers, veins, arteries and/or electrical pathways. For example, a prerequisite for performing a catheter ablation successfully is that the cause of the cardiac arrhythmia is accurately located in the heart chamber. Such locating may be done via an electrophysiological investigation during which electrical potentials are detected spatially resolved with a mapping catheter introduced into the heart chamber. This electrophysiological investigation, the so-called electro-anatomical mapping, thus provides 3D mapping data which can be displayed on a monitor. In many cases, the mapping function and a treatment function (e.g., ablation) are provided by a single catheter or group of catheters such that the mapping catheter also operates as a treatment (e.g., ablation) catheter at the same time. In this case, the scar tissue identifier can be directly stored and executed by the catheter 105.

Mapping of cardiac areas such as cardiac regions, tissue, veins, arteries and/or electrical pathways of the heart (e.g., 120) may result in identifying problem areas such as scar tissue, arrhythmia sources (e.g., electric rotors), healthy areas, and the like. Cardiac areas may be mapped such that a visual rendering of the mapped cardiac areas is provided using a display, as further disclosed herein. Additionally, cardiac mapping (which is an example of heart imaging) may include mapping based on one or more modalities such as, but not limited to local activation time (LAT), an electrical activity, a topology, a bipolar mapping, a dominant frequency, or an impedance. Data corresponding to multiple modalities may be captured using a catheter inserted into a patient's body and may be provided for rendering at the same time or at different times based on corresponding settings and/or preferences of a medical professional.

Cardiac mapping may be implemented using one or more techniques. As an example of a first technique, cardiac mapping may be implemented by sensing an electrical property of heart tissue, for example, LAT, as a function of the precise location within the heart. The corresponding data may be acquired with one or more catheters that are advanced into the heart using catheters that have electrical and location sensors in their distal tips. As specific examples, location and electrical activity may be initially measured on about 10 to about 20 points on the interior surface of the heart. These data points may be generally sufficient to generate a preliminary reconstruction or map of the cardiac surface to a satisfactory quality. The preliminary map may be combined with data taken at additional points in order to generate a more comprehensive map of the heart's electrical activity. In clinical settings, it is not uncommon to accumulate data at 1000 or more sites to generate a detailed, comprehensive map of heart chamber electrical activity. The generated detailed map may then serve as the basis for deciding on a therapeutic course of action, for example, tissue ablation, to alter the propagation of the heart's electrical activity and to restore normal heart rhythm.

Returning to FIG. 1, to implement the noted heart imaging, the medical professional 115 may insert a shaft 137 through a sheath 136, while manipulating a distal end of the shaft 137 using a manipulator 138 near the proximal end of the catheter 105 and/or deflection from the sheath 136. As shown in an inset 140, the catheter 105 may be fitted at the distal end of the shaft 137. The catheter 105 may be inserted through the sheath 136 in a collapsed state and may be then expanded within the heart 120. The catheter 105 may include at least one ablation electrode 134 and a catheter needle, as further disclosed herein.

According to embodiments, the catheter 105 may be configured to ablate tissue areas of a cardiac chamber of the heart 120. Inset 150 shows the catheter 105 in an enlarged view, inside a cardiac chamber of the heart 120. As shown, the catheter 105 may include the at least one ablation electrode 134 coupled onto the body of the catheter. According to other embodiments, multiple elements may be connected via splines that form the shape of the catheter 105. One or more other elements (not shown) may be provided and may be any elements configured to ablate or to obtain biometric data and may be electrodes, transducers, or one or more other elements.

According to embodiments disclosed herein, the ablation electrodes, such as the at least one ablation electrode 134, may be configured to provide energy to tissue areas of an intra-body organ such as heart 120. The energy may be thermal energy and may cause damage to the tissue area starting from the surface of the tissue area and extending into the thickness of the tissue area.

According to embodiments disclosed herein, biometric data may include one or more of LATs, electrical activity, topology, bipolar mapping, dominant frequency, impedance, or the like. The LAT may be a point in time of a threshold activity corresponding to a local activation, calculated based on a normalized initial starting point. Electrical activity may be any applicable electrical signals that may be measured based on one or more thresholds and may be sensed and/or augmented based on signal to noise ratios and/or other filters. A topology may correspond to the physical structure of a body part or a portion of a body part and may correspond to changes in the physical structure relative to different parts of the body part or relative to different body parts. Impedance may be the resistance measurement at a given area of a body part.

As shown in FIG. 1, the probe 110 and the catheter 105 may be connected to a console 160. The console 160 may include a computing device 161, which employs the scar tissue identifier as described herein. According to an embodiment, the console 160 and/or the computing device 161 include at least a processor and a memory, where the processor executes computer instructions with respect the scar tissue identifier described herein and the memory stores the instructions for execution by the processor.

The computing device 161 can be any computing device including software and/or hardware, such as a general-purpose computer, with suitable front end and interface circuits 162 for transmitting and receiving signals to and from the catheter 105, as well as for controlling the other components of system 100. The computing device 161 may include real-time noise reduction circuitry typically configured as a field programmable gate array (FPGA), followed by an analog-to-digital (A/D) electrocardiograph or electromyogram (EMG) signal conversion integrated circuit. The computing device 161 may pass the signal from an A/D ECG or EMG circuit to another processor and/or can be programmed to perform one or more functions disclosed herein. For example, the one or more functions include receiving a first modality and a second modality; cross referencing the first modality and the second modality; and generating improved image data for the first modality based on the cross referencing. The front end and interface circuits 162 include input/output (I/O) communication interfaces that enables the console 160 to receive signals from and/or transfer signals to the at least one ablation electrode 134.

In some embodiments, the computing device 161 may be further configured to receive biometric data, such as electrical activity, and determine if a given tissue area conducts electricity. According to an embodiment, the computing device 161 may be external to the console 160 and may be located, for example, in the catheter, in an external device, in a mobile device, in a cloud-based device, or may be a standalone processor.

As noted above, the computing device 161 may include a general-purpose computer, which may be programmed in software to carry out the functions of the scar tissue identifier described herein. The software may be downloaded to the general-purpose computer in electronic form, over a network, for example, or it may, alternatively or additionally, be provided and/or stored on non-transitory tangible media, such as magnetic, optical, or electronic memory (e.g., any suitable volatile and/or non-volatile memory, such as random-access memory or a hard disk drive). The example configuration shown in FIG. 1 may be modified to implement the embodiments disclosed herein. The disclosed embodiments may similarly be applied using other system components and settings. Additionally, system 100 may include additional components, such as elements for sensing electrical activity, wired or wireless connectors, processing and display devices, or the like.

According to an embodiment, a display 165 is connected to the computing device 161. During a procedure, the computing device 161 may facilitate the presentation of a body part rendering to the medical professional 115 on a display 165, and store data representing the body part rendering in a memory. In some embodiments, the medical professional 115 may be able to manipulate the body part rendering using one or more input devices such as a touch pad, a mouse, a keyboard, a gesture recognition apparatus, or the like. For example, an input device may be used to change a position of the catheter 105, such that rendering is updated. In alternative embodiments, the display 165 may include a touchscreen that can be configured to accept inputs from the medical professional 115, in addition to presenting the body part rendering. Note that the display 165 may be located at a same location or a remote location such as a separate hospital or in separate healthcare provider networks. Additionally, the system 100 may be part of a surgical system that is configured to obtain anatomical and electrical measurements of a patient's organ, such as the heart 120, and performing a cardiac ablation procedure. An example of such a surgical system is the Carto® system sold by Biosense Webster.

The console 160 may be connected, by a cable, to body surface electrodes, which may include adhesive skin patches that are affixed to the patient 125. The processor, in conjunction with a current tracking module, may determine position coordinates of the catheter 105 inside the body part (e.g., the heart 120) of the patient 125. The position coordinates may be based on impedances or electromagnetic fields measured between the body surface electrodes and the electrode or other electromagnetic components (e.g., the at least one ablation electrode 134) of the catheter 105. Additionally, or alternatively, location pads may be located on a surface of bed 130 and may be separate from the bed 130.

The system 100 may also, and optionally, obtain biometric data such as anatomical measurements of the heart 120 using ultrasound, computed tomography (CT), MRI, or other medical imaging techniques known in the art. The system 100 may obtain ECGs or electrical measurements using catheters or other sensors that measure electrical properties of the heart 120. The biometric data including anatomical and electrical measurements may then be stored in a non-transitory tangible media of the console 160. The biometric data may be transmitted to the computing device 161 from the non-transitory tangible media. Alternatively, or in addition, the biometric data may be transmitted to a server, which may be local or remote, using a network as further described herein.

According to one or more embodiments, catheters containing position sensors may be used to determine the trajectory of points on the cardiac surface. These trajectories may be used to infer motion characteristics such as the contractility of the tissue. Maps depicting such motion characteristics may be constructed when the trajectory information is sampled at a sufficient number of points in the heart 120.

Electrical activity at a point in the heart 120 may be typically measured by advancing the catheter 105 containing an electrical sensor at or near its distal tip (e.g., the at least one ablation electrode 134) to that point in the heart 120, contacting the tissue with the sensor and acquiring data at that point. One drawback with mapping a cardiac chamber using the catheter 105 containing only a single, distal tip electrode is the long period of time required to accumulate data on a point-by-point basis over the requisite number of points required for a detailed map of the chamber as a whole. Accordingly, multiple-electrode catheters have been developed to simultaneously measure electrical activity at multiple points in the heart chamber.

Multiple-electrode catheters may be implemented using any applicable shape such as a linear catheter with multiple electrodes, a balloon catheter including electrodes dispersed on multiple spines that shape the balloon, a lasso or loop catheter with multiple electrodes, or any other applicable shape. Linear catheters may be fully or partially elastic such that it can twist, bend, and or otherwise change its shape based on received signal and/or based on application of an external force (e.g., cardiac tissue) on the linear catheter. The balloon catheter may be designed such that when deployed into a patient's body, its electrodes may be held in intimate contact against an endocardial surface. As an example, a balloon catheter may be inserted into a lumen, such as a pulmonary vein (PV). The balloon catheter may be inserted into the PV in a deflated state such that the balloon catheter does not occupy its maximum volume while being inserted into the PV. The balloon catheter may expand while inside the PV such those electrodes on the balloon catheter are in contact with an entire circular section of the PV. Such contact with an entire circular section of the PV, or any other lumen, may enable efficient mapping and/or ablation.

According to an example, a multi-electrode catheter may be advanced into a chamber of the heart 120. Anteroposterior (AP) and lateral fluorograms may be obtained to establish the position and orientation of each of the electrodes. EGMs may be recorded from each of the electrodes in contact with a cardiac surface relative to a temporal reference such as the onset of the P-wave in sinus rhythm from a body surface ECG. The system, as further disclosed herein, may differentiate between those electrodes that register electrical activity and those that do not due to absence of close proximity to the endocardial wall. After initial EGMs are recorded, the catheter may be repositioned, and fluorograms and EGMs may be recorded again. An electrical map may then be constructed from iterations of the process above.

According to an example, cardiac mapping may be generated based on detection of intracardiac electrical potential fields. A non-contact technique to simultaneously acquire a large amount of cardiac electrical information may be implemented. For example, a catheter having a distal end portion may be provided with a series of sensor electrodes distributed over its surface and connected to insulated electrical conductors for connection to signal sensing and processing means. The size and shape of the end portion may be such that the electrodes are spaced substantially away from the wall of the cardiac chamber. Intracardiac potential fields may be detected during a single cardiac beat. According to an example, the sensor electrodes may be distributed on a series of circumferences lying in planes spaced from each other. These planes may be perpendicular to the major axis of the end portion of the catheter. At least two additional electrodes may be provided adjacent at the ends of the major axis of the end portion. As a more specific example, the catheter may include four circumferences with eight electrodes spaced equiangularly on each circumference. Accordingly, in this specific implementation, the catheter may include at least 34 electrodes (32 circumferential and 2 end electrodes).

According to another example, an electrophysiological cardiac mapping system and technique based on a non-contact and non-expanded multi-electrode catheter may be implemented. EGMs may be obtained with catheters having multiple electrodes (e.g., between 42 to 122 electrodes). According to this implementation, knowledge of the relative geometry of the probe and the endocardium may be obtained such as by an independent imaging modality such as transesophageal echocardiography. After the independent imaging, non-contact electrodes may be used to measure cardiac surface potentials and construct maps therefrom. This technique may include the following steps (after the independent imaging step): (a) measuring electrical potentials with a plurality of electrodes disposed on a probe positioned in the heart 120; (b) determining the geometric relationship of the probe surface and the endocardial surface; (c) generating a matrix of coefficients representing the geometric relationship of the probe surface and the endocardial surface; and (d) determining endocardial potentials based on the electrode potentials and the matrix of coefficients.

According to another example, a technique and apparatus for mapping the electrical potential distribution of a heart chamber may be implemented. An intra-cardiac multi-electrode mapping catheter assembly may be inserted into a patient's heart 120. The mapping catheter assembly may include a multi-electrode array with an integral reference electrode, or, preferably, a companion reference catheter. The electrodes may be deployed in the form of a substantially spherical array. The electrode array may be spatially referenced to a point on the endocardial surface by the reference electrode or by the reference catheter which is brought into contact with the endocardial surface. The preferred electrode array catheter may carry a number of individual electrode sites (e.g., at least 24). Additionally, this example technique may be implemented with knowledge of the location of each of the electrode sites on the array, as well as knowledge of the cardiac geometry. These locations are preferably determined by a technique of impedance plethysmography.

According to another example, a heart mapping catheter assembly may include an electrode array defining a number of electrode sites. The mapping catheter assembly may also include a lumen to accept a reference catheter having a distal tip electrode assembly which may be used to probe the heart wall. The mapping catheter may include a braid of insulated wires, and each of the wires may be used to form electrode sites. The catheter may be readily positionable in a heart 120 to be used to acquire electrical activity information from a first set of non-contact electrode sites and/or a second set of in-contact electrode sites.

According to another example, another catheter for mapping electrophysiological activity within the heart may be implemented. The catheter body may include a distal tip which is adapted for delivery of a stimulating pulse for pacing the heart or an ablative electrode for ablating tissue in contact with the tip. The catheter may further include at least one pair of orthogonal electrodes to generate a difference signal indicative of the local cardiac electrical activity adjacent the orthogonal electrodes.

According to another example, a process for measuring electrophysiologic data in a heart chamber may be implemented. The method may include, in part, positioning a set of active and passive electrodes into the heart 120, supplying current to the active electrodes, thereby generating an electric field in the heart chamber, and measuring the electric field at the passive electrode sites. The passive electrodes are contained in an array positioned on an inflatable balloon of a balloon catheter. In preferred embodiments, the array is said to have from 60 to 64 electrodes.

According to another example, cardiac mapping may be implemented using one or more ultrasound transducers. The ultrasound transducers may be inserted into a patient's heart 120 and may collect a plurality of ultrasound slices (e.g., two dimensional or three-dimensional slices) at various locations and orientations within the heart 120. The location and orientation of a given ultrasound transducer may be known and the collected ultrasound slices may be stored such that they can be displayed at a later time. One or more ultrasound slices corresponding to the position of a probe (e.g., a treatment catheter) at the later time may be displayed and the probe may be overlaid onto the one or more ultrasound slices.

According to other examples, body patches and/or body surface electrodes may be positioned on or proximate to a patient's body. A catheter with one or more electrodes may be positioned within the patient's body (e.g., within the patient's heart 120) and the position of the catheter may be determined by a system based on signals transmitted and received between the one or more electrodes of the catheter and the body patches and/or body surface electrodes. Additionally, the catheter electrodes may sense biometric data (e.g., LAT values) from within the body of the patient (e.g., within the heart 120). The biometric data may be associated with the determined position of the catheter such that a rendering of the patient's body part (e.g., heart 120) may be displayed and may show the biometric data overlaid on a shape of the body.

Figure 2:
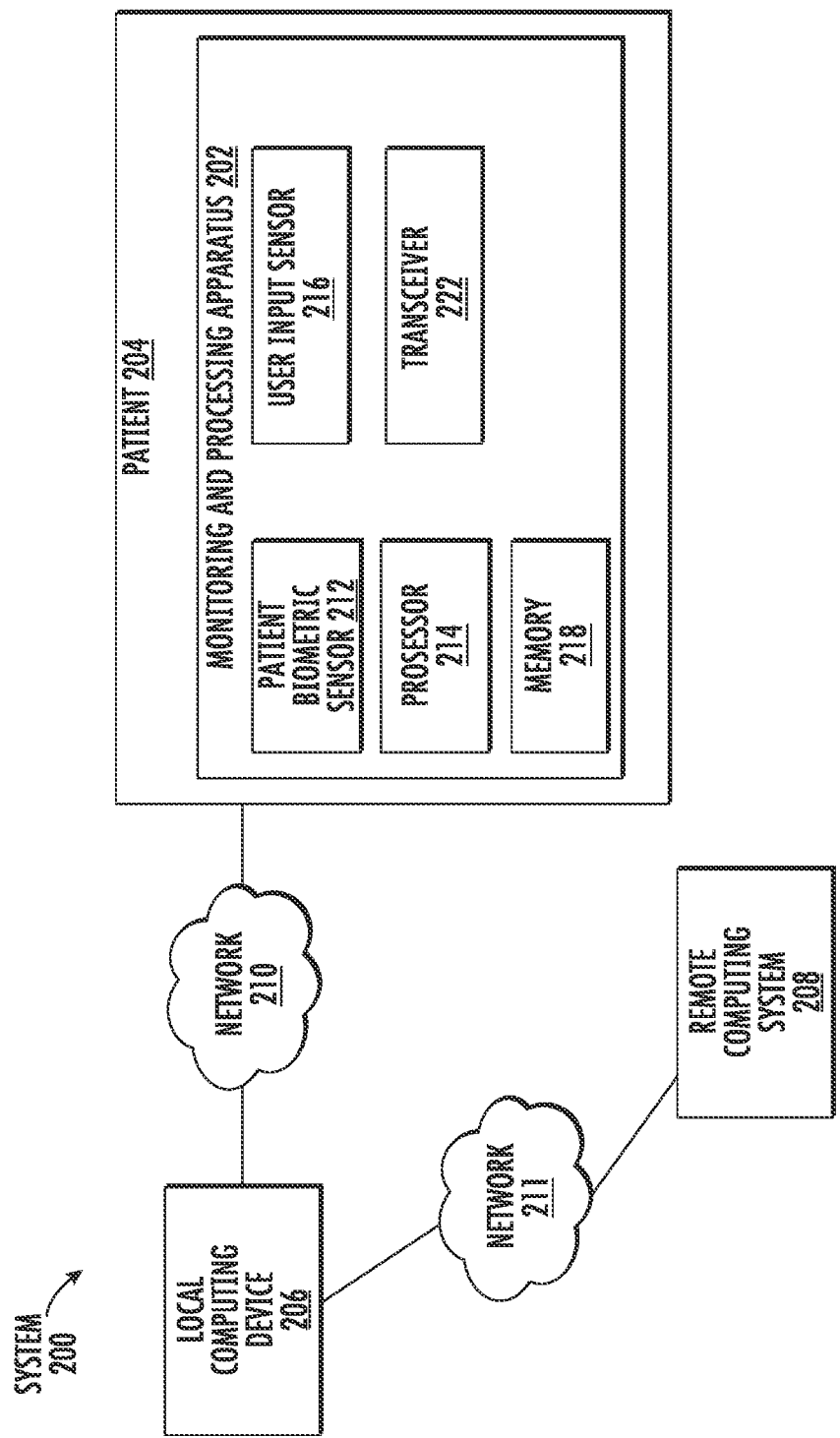
FIG. 2 illustrates a block diagram of an example system for remotely monitoring and communicating patient biometrics.

Turning now to FIG. 2, a block diagram of an example system 200 for remotely monitoring and communicating biometric data (i.e., patient biometrics, patient data, or patient biometric data) is illustrated. In the example illustrated in FIG. 2, the system 200 includes a monitoring and processing apparatus 202 (i.e., a patient data monitoring and processing apparatus) associated with a patient 204, a local computing device 206, a remote computing system 208, a first network 210, and a second network 211. In accordance with one or more embodiments, the monitoring and processing apparatus 202 can be an example of the catheter 105 of FIG. 1, the patient 204 can be an example of the patient 125 of FIG. 1, and the local computing device 206 can be an example of the console 160 of FIG. 1.

The monitoring and processing apparatus 202 includes a patient biometric sensor 212, a processor 214, a user input (UI) sensor 216, a memory 218, and a transmitter-receiver (i.e., transceiver) 222. In operation, the monitoring and processing apparatus 202 acquires biometric data of the patient 204 (e.g., electrical signals, blood pressure, temperature, blood glucose level or other biometric data) and/or receives at least a portion of the biometric data representing any acquired patient biometrics and additional information associated with any acquired patient biometrics from the one or more other patient biometric monitoring and processing apparatuses. The additional information may be, for example, diagnosis information and/or additional information obtained from an additional device such as a wearable device. The monitoring and processing apparatus 202 may employ the scar tissue identifier described herein to process data, including the acquired biometric data as well as any biometric data received from the one or more other patient biometric monitoring and processing apparatuses. For example, when processing data in this regard, the scar tissue identifier includes receiving a first modality and a second modality; cross referencing the first modality and the second modality; and generating improved image data for the first modality based on the cross referencing.

The monitoring and processing apparatus 202 may continually or periodically monitor, store, process, and communicate, via network 210, any number of various patient biometrics (e.g., the acquired biometric data). As described herein, examples of patient biometrics include electrical signals (e.g., ECG signals and brain biometrics), blood pressure data, blood glucose data, and temperature data. The patient biometrics may be monitored and communicated for treatment across any number of various diseases, such as cardiovascular diseases (e.g., arrhythmias, cardiomyopathy, and coronary artery disease) and autoimmune diseases (e.g., type I and type II diabetes).

The patient biometric sensor 212 may include, for example, one or more transducers configured to convert one or more environmental conditions into an electrical signal, such that different types of biometric data are acquired. For example, the patient biometric sensor 212 may include one or more of an electrode configured to acquire electrical signals (e.g., heart signals, brain signals, or other bioelectrical signals), a temperature sensor (e.g., thermocouple), a blood pressure sensor, a blood glucose sensor, a blood oxygen sensor, a pH sensor, an accelerometer, and a microphone.

As described in more detail herein, the monitoring and processing apparatus 202 may implementing a scar tissue identifier to receive at least images, data, and the like (e.g., instances of which can be referred to generally as modalities) from a single and/or multiple patients. The modalities can be of one or more types, such as an ultrasound type, a computed tomography (CT) type, an MRI type, or other medical imaging/scanning types. For example, a first modality can be of a first type, and a second modality can be of a second type that is different from the first type. The monitoring and processing apparatus 202 may implement a scar tissue identifier to cross reference the first modality and the second modality and generate improved image data for the first modality based on the cross referencing. Note that the improved image data includes enhanced accuracy over or higher resolution than original data of the first modality.

In another example, the monitoring and processing apparatus 202 may be an ECG monitor for monitoring ECG signals of a heart (e.g., the heart 120 of FIG. 1). In this regard, the patient biometric sensor 212 of the ECG monitor may include one or more electrodes (e.g., electrodes of the catheter 105 of FIG. 1) for acquiring ECG signals. The ECG signals may be used for treatment of various cardiovascular diseases.

In another example, the monitoring and processing apparatus 202 may be a continuous glucose monitor (CGM) for continuously monitoring blood glucose levels of a patient on a continual basis for treatment of various diseases, such as type I and type II diabetes. In this regard, the patient biometric sensor 212 of the CGM may include a subcutaneously disposed electrode (e.g., electrodes of the catheter 105 of FIG. 1), which may monitor blood glucose levels from interstitial fluid of the patient. The CGM may be, for example, a component of a closed-loop system in which the blood glucose data is sent to an insulin pump for calculated delivery of insulin without user intervention.

The processor 214 may be configured to receive, process, and manage, biometric data acquired by the patient biometric sensor 212, and communicate the biometric data to the memory 218 for storage and/or across the network 210 via the transceiver 222. Data from one or more other monitoring and processing apparatus 202 may also be received by the processor 214 through the transceiver 222, as described in more detail herein. Also, as described in more detail herein, the processor 214 may be configured to respond selectively to different tapping patterns (e.g., a single tap or a double tap) received from the UI sensor 216 (e.g., a capacitive sensor therein), such that different tasks of a patch (e.g., acquisition, storing, or transmission of data) may be activated based on the detected pattern. In some embodiments, the processor 214 can generate audible feedback with respect to detecting a gesture.

The UI sensor 216 includes, for example, a piezoelectric sensor or a capacitive sensor configured to receive a user input, such as a tapping or touching. For example, UI sensor 216 may be controlled to implement a capacitive coupling, in response to tapping or touching a surface of the monitoring and processing apparatus 202 by the patient 204. Gesture recognition may be implemented via any one of various capacitive types, such as resistive capacitive, surface capacitive, projected capacitive, surface acoustic wave, piezoelectric and infra-red touching. Capacitive sensors may be disposed at a small area or over a length of the surface, such that the tapping or touching of the surface activates the monitoring device.

The memory 218 is any non-transitory tangible media, such as magnetic, optical, or electronic memory (e.g., any suitable volatile and/or non-volatile memory, such as random-access memory or a hard disk drive).

The transceiver 222 may include a separate transmitter and a separate receiver. Alternatively, the transceiver 222 may include a transmitter and receiver integrated into a single device.

According to an embodiment, the monitoring and processing apparatus 202 may be an apparatus that is internal to a body of the patient 204 (e.g., subcutaneously implantable). The monitoring and processing apparatus 202 may be inserted into the patient 204 via any applicable manner including orally injecting, surgical insertion via a vein or artery, an endoscopic procedure, or a laparoscopic procedure.

According to an embodiment, the monitoring and processing apparatus 202 may be an apparatus that is external to the patient 204. For example, as described in more detail herein, the monitoring and processing apparatus 202 may include an attachable patch (e.g., that attaches to a patient's skin). The monitoring and processing apparatus 202 may also include a catheter with one or more electrodes, a probe, a blood pressure cuff, a weight scale, a bracelet or smart watch biometric tracker, a glucose monitor, a continuous positive airway pressure (CPAP) machine or virtually any device which may provide an input concerning the health or biometrics of the patient.

According to an embodiment, a monitoring and processing apparatus 202 may include both components that are internal to the patient and components that are external to the patient.

While a single monitoring and processing apparatus 202 is shown in FIG. 2, example systems may include a plurality of patient biometric monitoring and processing apparatuses. For instance, the monitoring and processing apparatus 202 may be in communication with one or more other patient biometric monitoring and processing apparatuses. Additionally, or alternatively, the one or more other patient biometric monitoring and processing apparatus may be in communication with the network 210 and other components of the system 200.

The local computing device 206 and/or the remote computing system 208, along with the monitoring and processing apparatus 202, can be any combination of software and/or hardware that individually or collectively store, execute, and implement the scar tissue identifier and functions thereof. Further, the local computing device 206 and/or the remote computing system 208, along with the monitoring and processing apparatus 202, can be an electronic, computer framework including and/or employing any number and combination of computing device and networks utilizing various communication technologies, as described herein. The local computing device 206 and/or the remote computing system 208, along with the monitoring and processing apparatus 202, can be easily scalable, extensible, and modular, with the ability to change to different services or reconfigure some features independently of others.

According to an embodiment, the local computing device 206 and the remote computing system 208, along with the monitoring and processing apparatus 202, include at least a processor and a memory, where the processor executes computer instructions with respect the scar tissue identifier and the memory stores the instructions for execution by the processor.

The local computing device 206 of system 200 is in communication with the monitoring and processing apparatus 202 and may be configured to act as a gateway to the remote computing system 208 through the second network 211. The local computing device 206 may be, for example, a, smart phone, smartwatch, tablet or other portable smart device configured to communicate with other devices via network 211. Alternatively, the local computing device 206 may be a stationary or standalone device, such as a stationary base station including, for example, modem and/or router capability, a desktop or laptop computer using an executable program to communicate information between the processing apparatus 202 and the remote computing system 208 via the PC's radio module, or a USB dongle. Biometric data may be communicated between the local computing device 206 and the monitoring and processing apparatus 202 using a short-range wireless technology standard (e.g., Bluetooth, Wi-Fi, ZigBee, Z-wave and other short-range wireless standards) via the short-range wireless network 210, such as a local area network (LAN) (e.g., a personal area network (PAN)). In some embodiments, the local computing device 206 may also be configured to display the acquired patient electrical signals and information associated with the acquired patient electrical signals, as described in more detail herein.

In some embodiments, the remote computing system 208 may be configured to receive at least one of the monitored patient biometrics and information associated with the monitored patient via network 211, which is a long-range network. For example, if the local computing device 206 is a mobile phone, network 211 may be a wireless cellular network, and information may be communicated between the local computing device 206 and the remote computing system 208 via a wireless technology standard, such as any of the wireless technologies mentioned above. As described in more detail herein, the remote computing system 208 may be configured to provide (e.g., visually display and/or aurally provide) the at least one of the patient biometrics and the associated information to a medical professional, a physician, a healthcare professional, or the like.

In FIG. 2, the network 210 is an example of a short-range network (e.g., local area network (LAN), or personal area network (PAN)). Information may be sent, via short-range network 210, between the monitoring and processing apparatus 202 and the local computing device 206 using any one of various short-range wireless communication protocols, such as Bluetooth, Wi-Fi, Zigbee, Z-Wave, near field communications (NFC), ultraband, Zigbee, or infrared (IR).

The network 211 may be a wired network, a wireless network or include one or more wired and wireless networks, such as an intranet, a local area network (LAN), a wide area network (WAN), a metropolitan area network (MAN), a direct connection or series of connections, a cellular telephone network, or any other network or medium capable of facilitating communication between the local computing device 206 and the remote computing system 208. Information may be sent, via the network 211 using any one of various long-range wireless communication protocols (e.g., TCP/IP, HTTP, 3G, 4G/LTE, or 5G/New Radio). Wired connections may be implemented using Ethernet, Universal Serial Bus (USB), RJ-11 or any other wired connection generally known in the art. Wireless connections may be implemented using Wi-Fi, WiMAX, and Bluetooth, infrared, cellular networks, satellite or any other wireless connection methodology. Additionally, several networks may work alone or in communication with each other to facilitate communication in the network 211. In some instances, the remote computing system 208 may be implemented as a physical server on the network 211. In other instances, the remote computing system 208 may be implemented as a virtual server a public cloud computing provider (e.g., Amazon Web Services (AWS)®) of the network 211.

Figure 3:
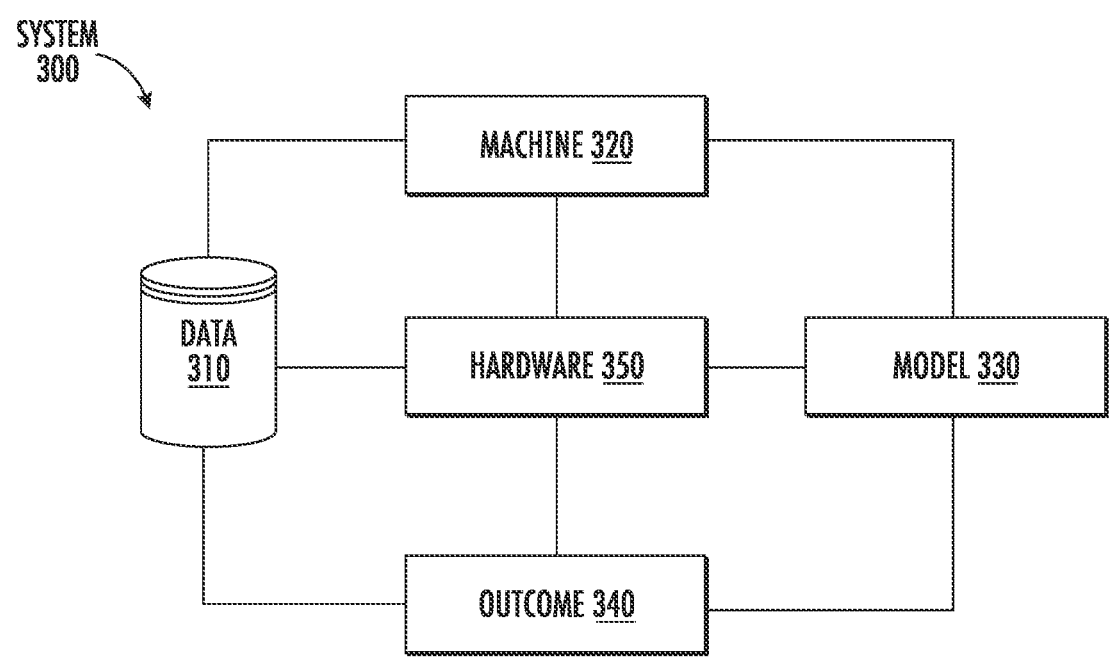
FIG. 3 illustrates a graphical depiction of an artificial intelligence system.
Figure 4:
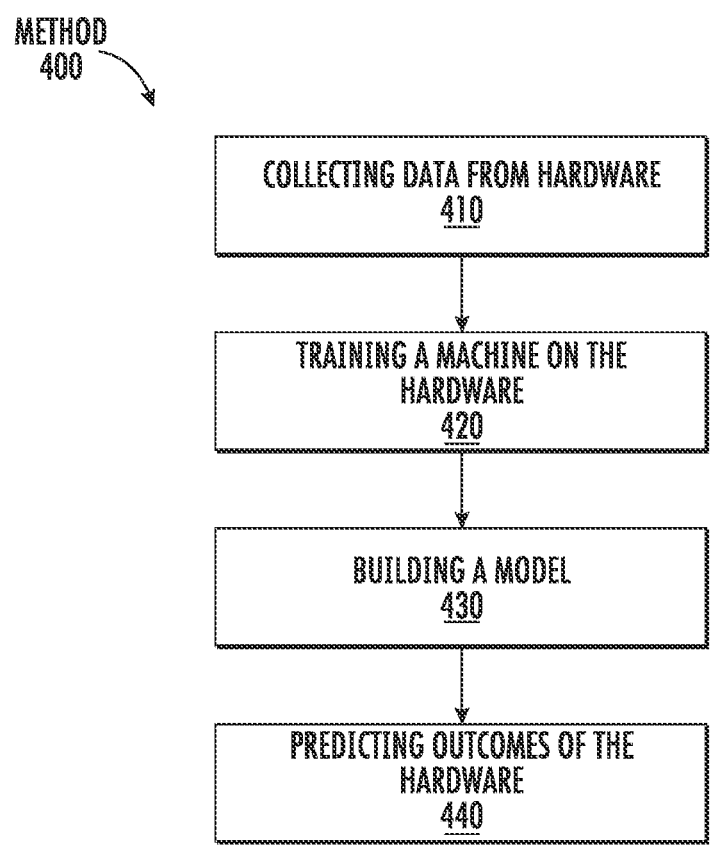
FIG. 4 illustrates a block diagram of a method performed in the artificial intelligence system of FIG. 3.

FIG. 3 illustrates a graphical depiction of an artificial intelligence system 300 according to one or more embodiments. The artificial intelligence system 300 includes data 310, a machine 320, a model 330, a plurality of outcomes 340, and underlying hardware 350. FIG. 4 illustrates a block diagram of a method 400 performed in the artificial intelligence system of FIG. 3. The description of FIGS. 3-4 is made with reference to FIG. 2 for ease of understanding.

In general, the artificial intelligence system 300 operates the method 400 by using the data 310 to train the machine 320 (e.g., the local computing device 206 of FIG. 2) while building the model 330 to enable the plurality of outcomes 340 (to be predicted). In such a configuration, the artificial intelligence system 300 may operate with respect to the hardware 350 (e.g., the monitoring and processing apparatus 202 of FIG. 2) to train the machine 320, build the model 330, and predict outcomes using algorithms. These algorithms may be used to solve the trained model 330 and predict outcomes 340 associated with the hardware 350. These algorithms may be divided generally into classification, regression, and clustering algorithms.

At block 410, the method 400 includes collecting the data 310 from the hardware 350. The machine 320 operates as the controller or data collection associated with the hardware 350 and/or is associated therewith. The data 310 (e.g., biometric data, which may originate with the monitoring and processing apparatus 202 of FIG. 2) may be related to the hardware 350. For instance, the data 310 may be on-going data, or output data associated with the hardware 350. The data 310 may also include currently collected data, historical data, or other data from the hardware 350. For example, the data 310 may include measurements during a surgical procedure and may be associated with an outcome of the surgical procedure. For example, a temperature of a heart (e.g., of the patient 204) or the dimensions of the heart chambers may be collected and correlated with an outcome of a heart procedure.

At block 420, the method 400 includes training the machine 320, such as with respect to the hardware 350350. The training may include an analysis and correlation of the data 310 collected at block 410. For example, in the case of the heart, the data 310 of temperature and outcome may be trained to determine if a correlation or link exists between the temperature of the heart (e.g., of the patient 204) during the heart procedure and the outcome.

At block 430, the method 400 includes building the model 330 on the data 310 associated with the hardware 350. Building the model 330 may include physical hardware or software modeling, algorithmic modeling, and/or the like. This modeling may seek to represent the data 310 that has been collected and trained. According to an embodiment, the model 330 may be configured to model the operation of hardware 350 and model the data 310 collected from the hardware 350 to predict the outcome achieved by the hardware 350. In accordance with one or more embodiments, the model 330, with respect to the scar tissue identifier, receives a first modality and a second modality; cross references the first modality and the second modality; and generates improved image data for the first modality based on the cross referencing.

At block 440, the method 400 includes predicting the plurality of outcomes 340 of the model 330 associated with the hardware 350. This prediction of the plurality of outcomes 340 may be based on the trained model 330. For example and to increase understanding of the disclosure, in the case of the heart, if the temperature during the procedure is between 36.5 degrees Celsius and 37.89 degrees Celsius (i.e., 97.7 degrees Fahrenheit and 100.2 degrees Fahrenheit) produces a positive result from the heart procedure, the outcome can be predicted in a given procedure based on the temperature of the heart during the heart procedure. Thus, using the outcome 340 that is predicted, the hardware 350 may be configured to provide a certain desired outcome 340 from the hardware 350.

Figure 5:
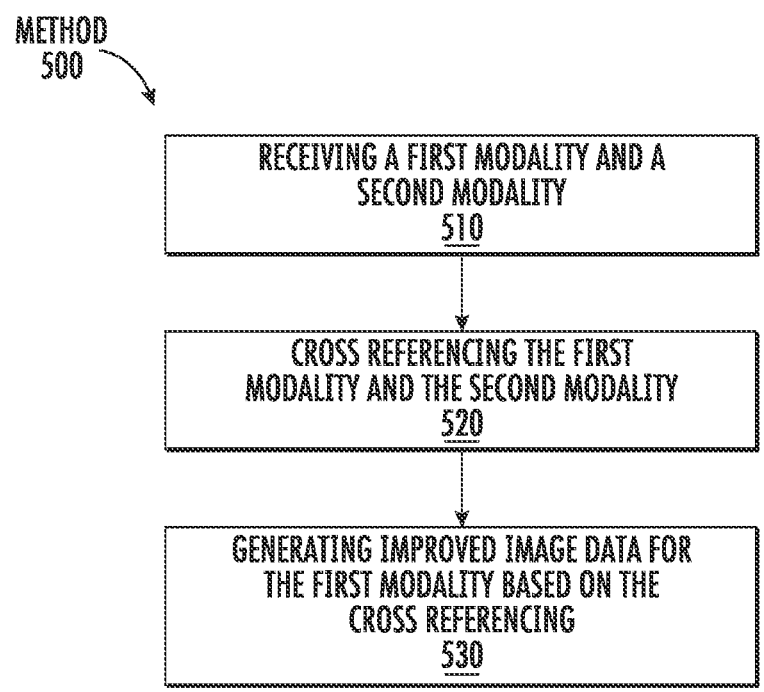
FIG. 5 illustrates a block diagram of a method of automatically identifying scar areas within organic tissue based on multiple imaging modalities.

Turning now to FIG. 5, a block diagram of a method 500 of automatically identifying scar areas within organic tissue based on multiple imaging modalities is illustrated according to one or more embodiments. In accordance with an embodiment, the method 500 is implemented by the system for identifying scar tissue. The system for identifying scar tissue may be embodied as a machine learning algorithm that cross references different modalities to strengthen findings of a single modality. Any combination of software and/or hardware (e.g., the local computing device 206 and the remote computing system 208, along with the monitoring and processing apparatus 202) can individually or collectively store, execute, and implement the system for identifying scar tissue and functions thereof. In general, the system for identifying scar tissue cross references different modalities to strengthen findings of a single modality, such that scar areas within organic tissue can be identified. For instance, the system for identifying scar tissue may be outcome oriented in that the machine learning software/hardware implements comparing, cross referencing, and identifying of subsequent modalities based on comparing, cross referencing, and identifying operations of prior modalities. The machine learning software/hardware may include, but is not limited to, neural networks, artificial neural networks, convoluted neural networks, encoders, decoders, tree-structures, and autoencoders.

The process flow 500 begins at block 510, where the system for identifying scar tissue receives a first modality and a second modality. In accordance with one or more embodiments, the first modality is representative of one or more first modalities each of which is of a first type. For example, the first modality may be an image or data underlying the image. In some cases, the data of the first modality may be considered original data. The second modality is of a second type that is different from the first type. Similarly, for example, the second modality may be an image or data underlying the image. The first type may be an ultrasound image or data thereof, while the second modality of the second type can be an LGE-MRI image or data thereof. The system for identifying scar tissue may receive the first modality and/or the second modality in real time from medical device equipment or may access the first modality and/or the second modality in a memory. The receiving may be automatic or user initiated.

At block 520, the system for identifying scar tissue cross references the first modality and the second modality. To cross reference the first modality and the second modality, the system for identifying scar tissue compares the first modality to the second modality. In this regard, the system for identifying scar tissue matches locations of the first modality to corresponding locations of the first modality. For example, ultrasound data can be mapped according to voltage to LGE-MRI data. In accordance with one or more embodiments, the cross referencing can be reciprocal between the modalities. That is, the first modality may improve the second modality, and the second modality may improve the first modality.

At block 530, the system for identifying scar tissue generates improved image data for the first modality based on the cross referencing. That is, once mapped, the system for identifying scar tissue adjusts and interprets the original data of the first modality based on the second modality to generate improved image data for the first modality. Thus, once adjusted and interpreted, the improved image data is more accurate and includes a higher resolution than the original data without relying on a human operator's subjective interpretation (as in conventional imaging modalities). In accordance with one or more embodiments, the first and second modalities may be utilized to generate/produce a hybrid modality utilizing the reciprocal nature of the cross-reference operation of block 520. The hybrid modality includes a combination of two or more modalities of two or more types (e.g., combined improved data) and, therefore, incorporates the reciprocal improvements that each modality type can provide to another modality. The first and second modalities may be patient specific, then, over time, subsequent modalities and/or secondary data (height, weight, heart disease, etc.) may be used by the process 500 and contribute to the combined improved data. Further, over time, the patient specific data, modalities, and/or secondary data may be used by the process 500 and contribute to the combined improved data for other patients.

Figure 6:
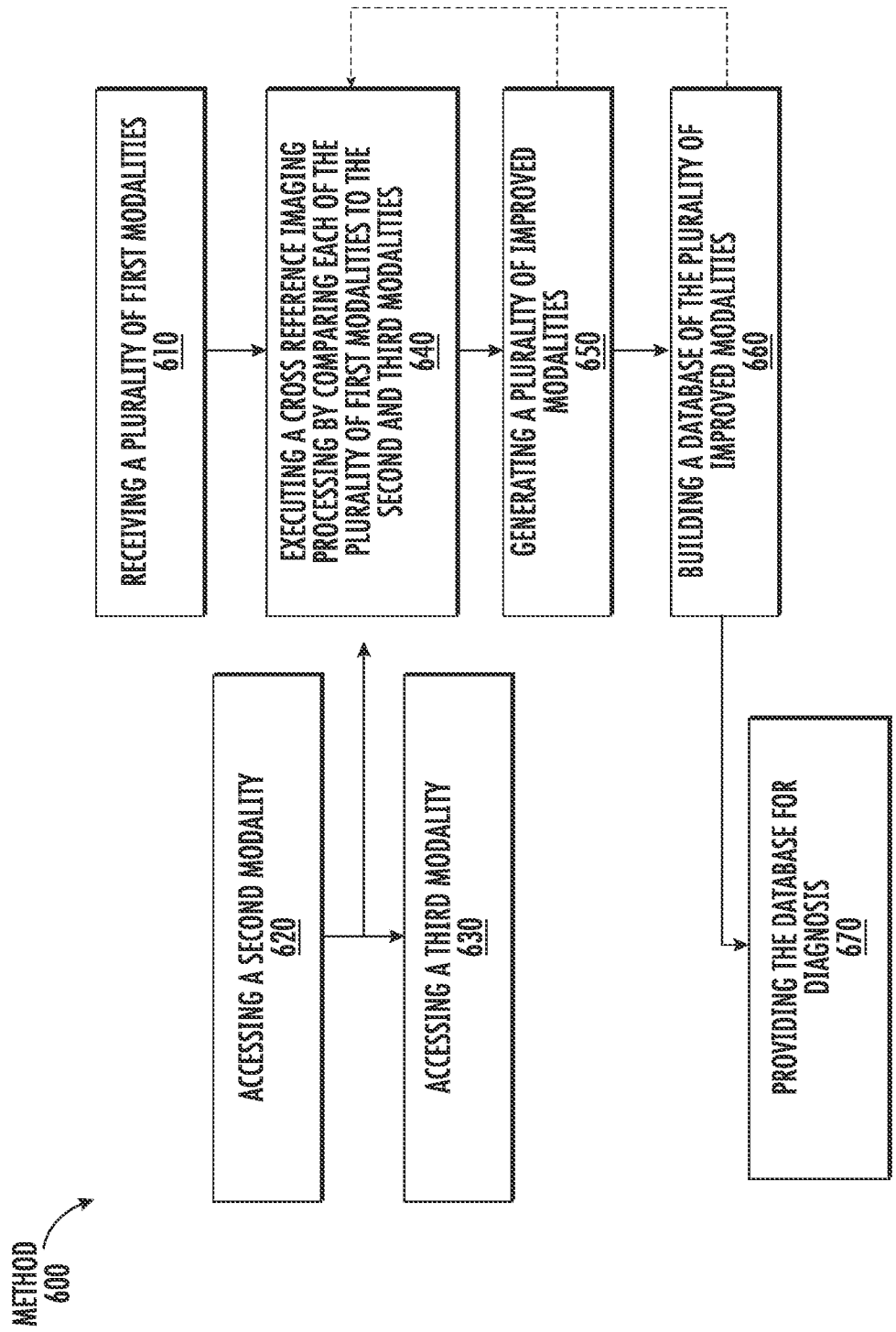
FIG. 6 illustrates a block diagram of a method of automatically identifying scar areas within organic tissue based on multiple imaging modalities.

FIG. 6 illustrates a block diagram of a method 600 of automatically identifying scar areas within organic tissue based on multiple imaging modalities according to one or more embodiments. In accordance with an embodiment, the method 600 is implemented by a system for identifying scar tissue. Any combination of software and/or hardware (e.g., the local computing device 206 and the remote computing system 208, along with the monitoring and processing apparatus 202) can individually or collectively store, execute, and implement the system for identifying scar tissue and functions thereof. In general, the system for identifying scar tissue cross references different modalities to strengthen findings of a single modality. For instance, with respect to a heart of a patient, by strengthening finding of the single modality, the system for identifying scar tissue may model existing scars and other hard to reach areas that catheters may not be able to detect. This modeling assists with diagnosis of heart diseases as described herein.

The method 600 begins at block 610, where the system for identifying scar tissue receives or accesses a first modality. In accordance with one or more embodiments, the system for identifying scar tissue receives or accesses a plurality of modalities of the first type. For example, data can be obtained from a specific type of sensor (e.g., a catheter, electrode, ultrasound transducer, medical database, etc.) from a patient. The first modality can be one of, or a combination of, ultrasound data, MRI data, and cardo data (e.g., a cardiac map) of a heart of the patient. In accordance with one or more embodiments, the first modality of the first type includes ultrasound data. The data may be stored and/or organized in any data structure (e.g., a table, a tree, a matrix, etc.) suitable for how the data was obtained and how the data functions.

At block 620, the system for identifying scar tissue receives or accesses a second modality. In accordance with one or more embodiments, the system for identifying scar tissue receives or accesses a plurality of modalities of the second type with respect to the heart of the patient (e.g., data can be obtained from a database within the local computing device 206 or the remote computing system 208 of FIG. 2). The second modality may be a second type that is different from the first type. In accordance with one or more embodiments, the second modality of the second type includes LGE-MRI data.

At block 630, the system for identifying scar tissue accesses a third modality. In accordance with one or more embodiments, the system for identifying scar tissue receives or accesses a plurality of modalities of the third type with respect to the heart of the patient (e.g., data can be obtained from a database within the local computing device 206 or the remote computing system 208 of FIG. 2). The third modality may be of a third type that is different from the first and second types. In accordance with one or more embodiments, the third modality of the third type includes a cardiac map.

At block 640, the system for identifying scar tissue cross references the first modality with the third and second modalities. This cross referencing includes comparing the first modality to the third and second modalities to corresponding locations, which provides redundancy for particular areas of the heart. In this way, data is correlated between modalities so that the second and third modalities complement the first modality and provide additional data for hard to reach areas. For instance, if the ultrasound data is considered base data with low resolution, by correlating the ultrasound data with the LGE-MRI data and cardiac map the system for identifying scar tissue creates a larger dataset for diagnosis. In accordance with one or more embodiments, the cross referencing may be reciprocal between the modalities. That is, the first, second, and third modalities may improve each other. Further, as the method 600 proceeds through multiple iterations, the cross referencing may utilize the improved modalities of blocks 650 and the database of block 660 to implement machine learning (as noted by the dashed arrow from blocks 650 and 660 to 640).

At block 650, the system for identifying scar tissue generates a plurality of improved modalities (e.g., corresponding data structures storing the generated data). In this regard, the original data of each of the first modalities is improved based on the cross referencing. For example, the system for identifying scar tissue adjusts and interprets to the original data of each of the first modalities based on the second and third modalities to generate the improved image data. The plurality of improved modalities includes improved image data that has enhance accuracy over and/or higher resolution compared original data of the first modality. The system for identifying scar tissue may generate corresponding improved images from the improved image data. In accordance with one or more embodiments, the first, second, and third modalities may be utilized to generate/produce a hybrid modality utilizing the reciprocal nature of the cross-reference operation of block 640.

In accordance with one or more embodiments, weights (e.g., alpha numeric values) may be assigned (e.g., associated within the data structure) to the original data and/or the improved image data of the modalities. Specifically, a highest weight may be attributed to an actual identification of scar tissue. Specifically, in an embodiment, multiple weights may be used including a first weight to indicate the severity of the scar tissue and a second weight to provide the likelihood of the first weight. In combination, the improved data is 'improved' because the data collects the benefits from each of the underlying modalities (e.g., ultrasound data enable depth of tissue analysis, the MRI data adds viability, and the cardiac mapping yields electrocardiogram data).

At block 660, a database is built using the improved image data and/or the improved images (including any hybrid modalities and/or weights). The improved image data may be used to create a new database as part of a training process or added to the database that houses the data of the modalities. In accordance with one or more embodiments, the database may be resident on a computing system (e.g., within the local computing device 206 or the remote computing system 208 of FIG. 2). The database may further include additional information from other patients, such as data collected from physicians and/or medical professionals, to support feature/optimizations.

At block 670, the database and the improved image data and/or the improved images therein are then provided to physicians and/or medical professionals. In turn, the physicians and/or medical professionals may utilize the improved image data and/or the improved images into one or more of ablation-ultrasound technologies, planning and diagnosis of lesions, and assessment and diagnosis of magnetic resonance to address a disease state. Specifically, an ability to diagnosis is enhanced by the improved image data and/or the improved images, as the improved image data and/or the improved images identifies scar tissue that otherwise would not be identified by conventional imaging modalities.

A system and method for producing a 3D model of cardiac chamber tissue that includes scar regions with a likelihood score based on inputs including a 3D Shell and at least one imaging modality. The at least one imaging modality may include one or more of a CT, MR or ULS image set. Additional inputs may include demographic data, electro-anatomical information from a 3D mapping system, and intracardiac and body surface related information disclosed in more detail below. The system and method output 3D voxels with a scar level score and a confidence in the score associated with each voxel.

Figure 7:
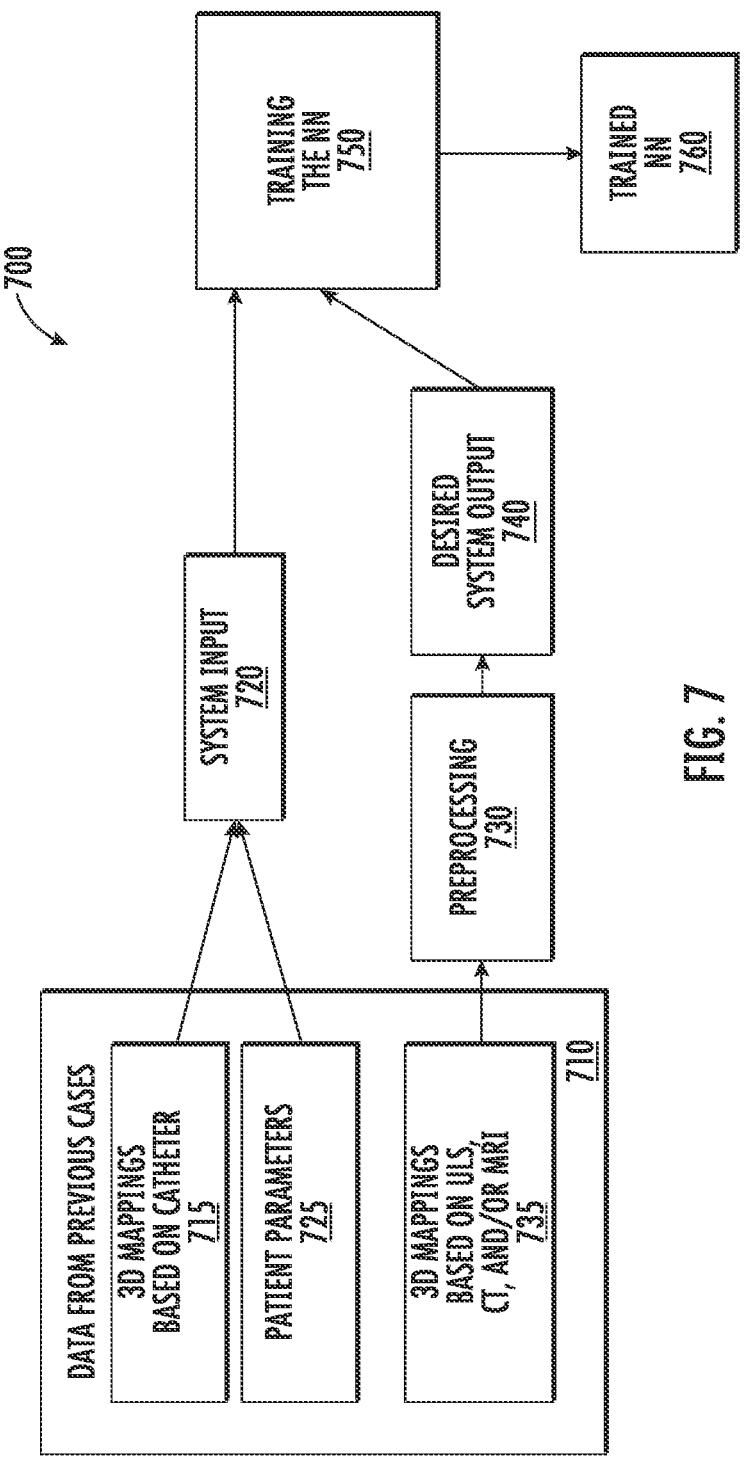
FIG. 7 illustrates the data preparation and training of the present system.

FIG. 7 illustrates the data preparation and training of the present system. Data from previous patient cases 710 is used for training the system for each such case. The data from previous patient cases 710 may include 3D mappings 735 (described in detail herein) and patient parameters 725 data (described in detail herein), such as age, gender, medical history, etc., and 3D mappings-based on the catheter 715. The data from previous clinical cases 710 including 3D mappings-based on the catheter 715 and patient parameters 725 data may to be used as a system input 720 to the system described herein and data to be used for calculation of the output and to train the system in training step 750.

Data from previous clinical cases 710 may include previous clinical cases that are relevant to train the system and algorithm. For each such case, available data should include inputs described herein, as well as patient ID 725 and data describing the outputs.

The data 735 to be used for calculation of the desired output 740 may include a 3D model of cardiac tissue, where each voxel has an indication of scar density at that voxel, based on data from LGE-MRI readings determined by an expert or an automatic tool. The data 735 to be used for calculation of the desired output 740 may include a 3D model of cardiac tissue, where each voxel has an indication of radiopacity and tissue elasticity at that voxel, based on data from Ultrasound readings determined by an expert or an automatic tool. The data 735 to be used for calculation of the desired output 740 may include a 3D model of cardiac tissue, where each voxel has an indication of radiopacity and tissue elasticity at that voxel, based on data from Delayed Enhancement CT readings determined by an expert or an automatic tool.

Preprocessing 730 may occur on the 3D mappings 735 to conform to the desired output form. The data 735 may be preprocessed to conform to the desired output 740 format where each voxel has a value between 0 and 1, indicating the density of the scar (1=most severe, no electricity passing, 0=no scar) and a confidence score. Calculating the confidence score may rely on manual scoring by an expert, on the 3D tissue model, based on the ULS/MRI/CT mappings 735, and/or automatic scoring by specifying a threshold—radiopacity scale for ULS/MRI/CT.

According to an embodiment, data 735 voxels with confidence score above 90% may be used while excluding or weighting lower confidence scores. Further, in an embodiment, data 710 may be expected to include at least 85% of the voxels having confidence scores above 90% to be included in the data 710. Other scores of lower confidence scores may be weighted or excluded. In an embodiment the confidence threshold is selected by the physician during the intraoperatively.

After preprocessing 730 on 3D mappings 735, the desired output 740 may be included and provided to training the neural network at step 750.

Once the training 750 occurs, the neural network is trained 760. The dataset may be split into a training set, a validation set, and a test set. The training and validation sets may be used during system development, while the test set is used for evaluating the system's accuracy. Cross-validation may be used to improve performance.

Figure 8:
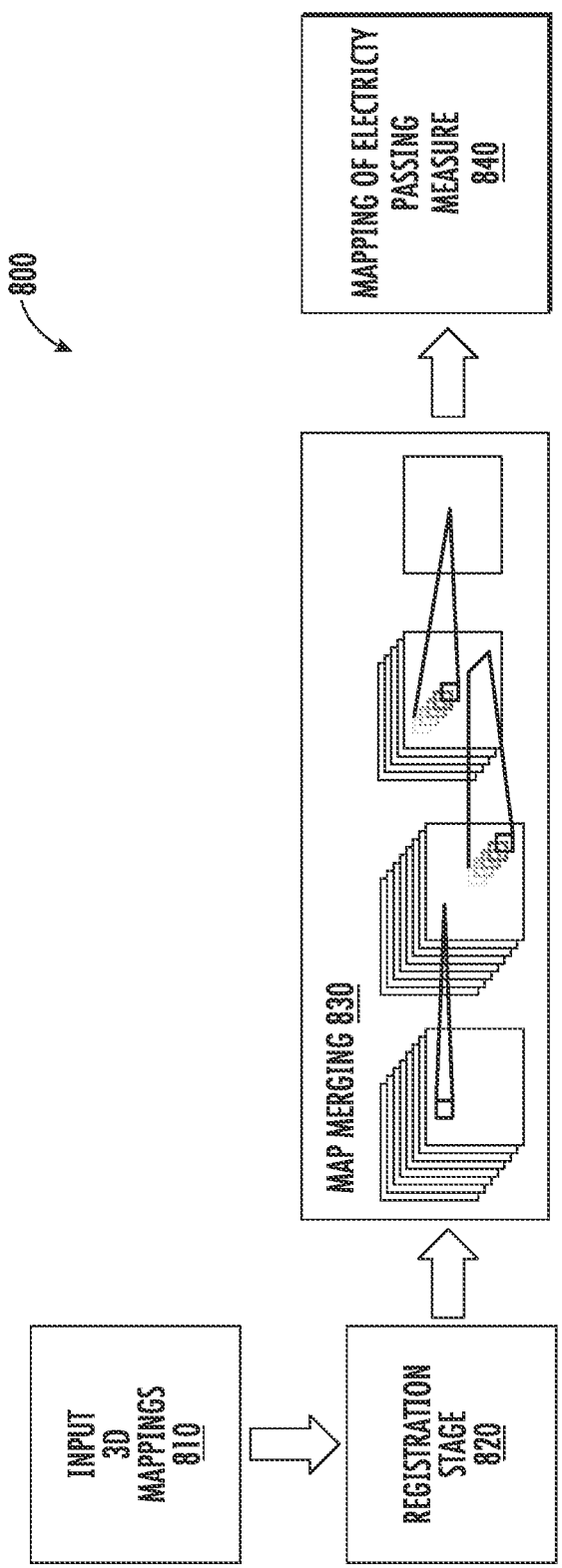
FIG. 8 illustrates an example architecture for the present system.
Figure 9:
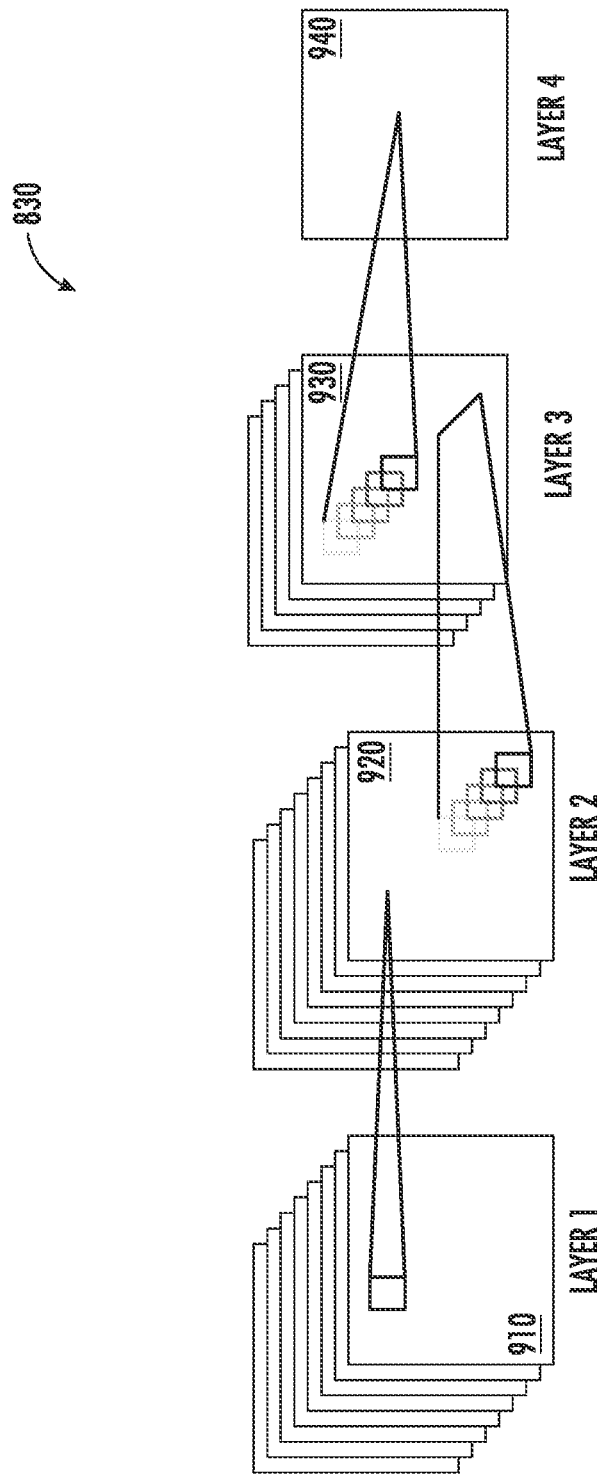
FIG. 9 illustrates a possible architecture for the map merging stage of FIG. 8.

FIGS. 8 and 9 illustrate an example combined architecture for the present system. The mappings may be input into the system at step 810 as described herein.

Registration of the mapping may occur in a registration stage 820. In order for the system to be able to learn patterns and generalize correctly given data from different patients' registration may be needed. Alignment of the various inputs with each other may be calculated—referred to as "registration." Registration in registration stage 820 may occur in various dimensions, including intra-patient alignment and inter-patient alignment.

For intra-patient alignment, according to an embodiment, if 3D mappings are produced from the catheter for both the epicardial and endocardial surfaces of the heart chamber, the registration may be inherent in the 3D mapping system capabilities. For example, in the CARTO®3, for example, maps collected during a case are registered. Other images, such as MRI, CT, and/or ULS, may need registration with the 3D catheter maps, and with other such images. For example, when the ULS images are collected by a navigated catheter, the ULS images may be automatically registered to the 3D map. Other registration techniques already described in the literature may also be used.

For inter-patient alignment, according to an embodiment, the data may be normalized to a "standard model" of the cardiac chamber. The various mappings are "projected" onto this standard model. The resulting projections may then be provided to the map merging stage 830.

Map merging 830 may occur and the output of a mapping of electricity passing may occur at step 840. There are many possible neural architectures as described herein that may be used in the map merging 830 to calculate the desired output. Some of these architectures are provided herein above and several detailed architectures are provided additionally below. More complex architectures may be desired, depending on the nature of the data.

As discussed above with respect to the registration stage 820, the input to the map merging stage 830 is the output of registration stage 820 that aligns the 3D input mappings to "standardized" 3D mappings. The input to the map merging stage 830 includes N mappings, each mapping being a 3D "cubic image" of size H×W×D with voxels (which are 3D "pixels"). Each voxel may have a plurality of values associated therewith including voltage, elasticity, scar from MR/CT, wall motion, for example.

According to one embodiment, the map merging stage 830 combines the input mappings using some linear combination. One neural layer of size H×W×D, where neuron (i,j,k) is fed the values in position (i,j,k) in each of the N cubic images may be used. This embodiment for the map merging stage 830 may be used when each voxel in each input map presents, by itself, a somewhat reliable indication for scar tissue, and provided that a simple linear combination (or averaging) of the input maps is sufficient for integration. Such an embodiment for the map merging stage 830 may be beneficial as being easy to train, with less data compared to more complex models. Such an embodiment for the map merging stage 830 may provide results that are not sufficiently accurate.

In order to gain accuracy and increase the benefit of the map merging 830, additional layers, i.e., a deeper network may be used. Additional layers may provide the ability to represent more complex functions. Larger layer may be used. Larger layers may allow the ability to capture more nuances in the data. Separate processing may also be used. Separate processing on each input map before combining the information may provide additional benefits. Additionally, or alternatively, different types of layer architectures, e.g., fully-connected, convolutional neural network (CNN), max-pooling, etc., as described herein may be used.

These techniques to gain accuracy and increase the benefit of map merging stage 830 are described below. Map merging stage 830 may be enhanced by utilizing two layers including a first ("hidden") layer of size H×W×D×k (i.e. a 3D layer H×W×D with "thickness" k>1), and a second ("output") layer of size H×W×D. Each of the k neurons in position (i,j,k) in the first layer is fed the N signals from position (i,j,k) from each of the N input maps, and its output is given to neuron (i,j,k) in the second layer. The non-linear combinations of the N values in each voxel may be represented.

Map merging stage 830 may be enhanced when considering a voxel in the given cubic area as a potential candidate for scar tissue, such a decision may depend on the input mapping values in the surrounding cubic region of the candidate voxel, rather than the entire mapping. The calculation may utilize standard art in deep learning using CNNs to gain the benefit of this surrounding region information.

Map merging stage 830 may be enhanced by, for example, providing each of the input N images may have its own convolutional model, namely each input image is fed into a separate CNN. Each convolution-filter in the CNN layer may utilize as its input a small cube of voxels, and outputs one value. The output of each CNN is a cubic image that gives a preliminary output recommendation map based on just one input mapping.

Additional layers may enhance the map merging stage 830 by applying on one of the N map "tracks" separately, according to deep learning for image/area processing using CNN, max-pooling, and other standard paradigms discussed herein as known by those possessing skill in the art.

A combining layer may be utilized to receive the input maps and/or the output of the previous separate-processing layers as described to combines the data into one representation. The combination may be performed using a simple linear combination, as explained herein, or using more complex combinations, namely non-linear combination, and/or CNN, max-pooling, and other standard layers of image processing.

FIG. 9 illustrates a possible architecture for map merging stage 830. For the purpose of graphical clarity, the architecture illustrates a NN that processes 2D images, but this idea can be applied in the same manner on 3D cubic images.

The input on the left consists of N=8 2D mappings (each representing the output of registration 820 on the inputs 810. Each such mapping is processed separately in Layer 1 910 by a different CNN grid. The output of layer 1 910 includes N=8 convoluted mappings, which are fed into Layer 2 920. These mappings are then fed into the combining Layer 3 930, described herein and above as a combing in layer, which has depth k=5 in order to allow for non-linear combinations, also described above. The k combined layers are merged into the output map by Layer 4 940. The values N=8 and k=5 here are merely example values and one possessing skill in the art would understand that may other values may be used. Additional, or fewer, layers may be used as compared to those illustrated, depending on the nature of the data and the required accuracy of the output.

Patient parameters, such as age, gender, medications, medical history and type of atrial fibrillation may affect the results. A separate model may be trained based on some of the input patient parameters. Alternatively, the patient inputs may be provided to the layers in the NN architecture to help it learn differences based on these parameters.

Hearts of different patients may be different, resulting in variations in the recorded data. According to an embodiment, the system may need to be trained in batches with each of the batches limited to the data of a single patient. Data needs to be collected from at least a certain number of patients for the system's training to be robust.

Even after the system is ready and is deployed in hospitals, additional data may be accumulated. The additional data may be added to the training dataset, and the system may be re-trained, to continually improve accuracy. Specifically, data from additional operations may provide feedback, by considering success ratings of ablations performed in accordance with the system's recommendations.

Figure 10:
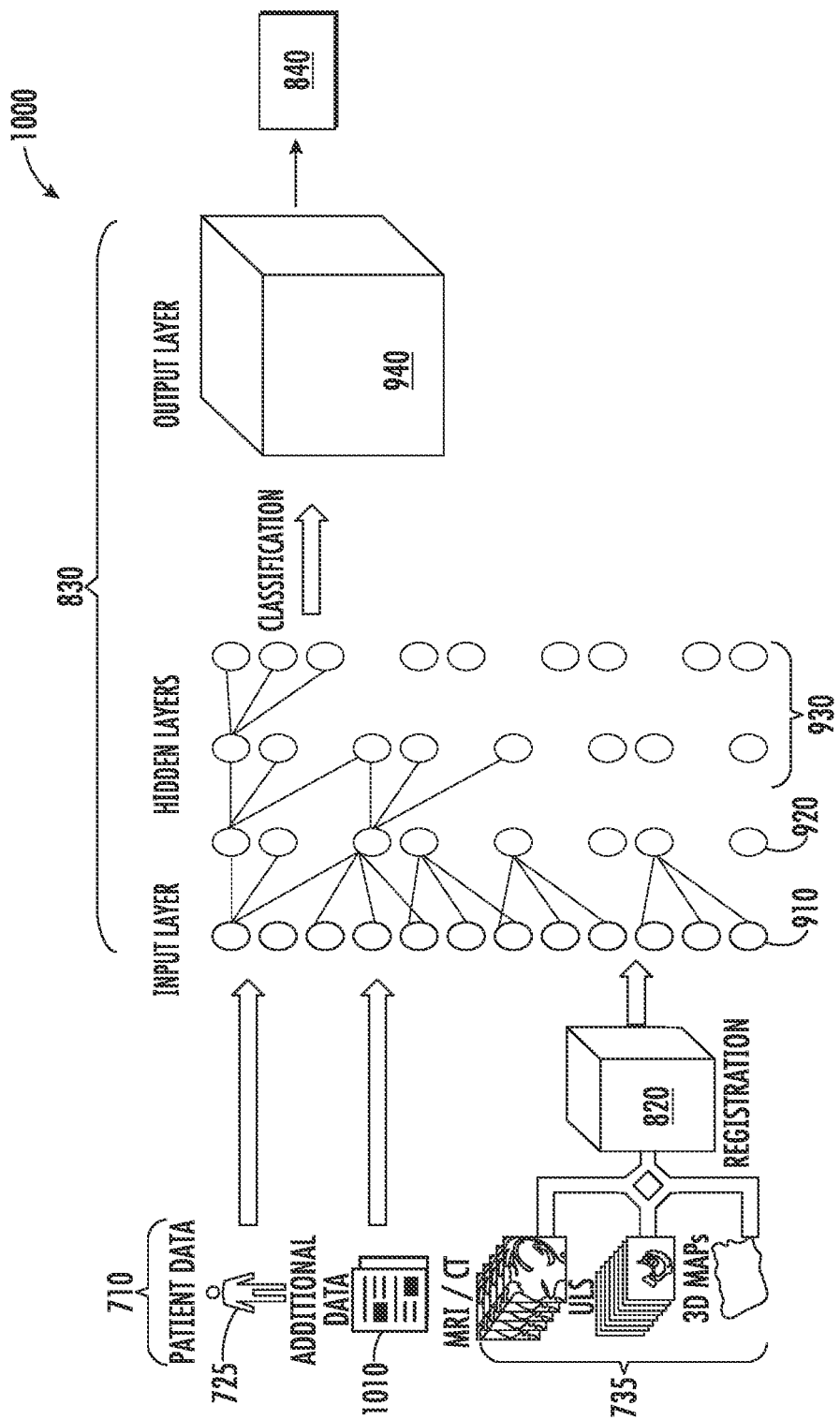
FIG. 10 illustrates a system using a neural network in accordance with the embodiments described herein.

FIG. 10 illustrates a system 1000 using a neural network in accordance with the embodiments described herein. System 1000 includes patient data 725, additional data 1010, and 3D mappings 735, including, for example, MRI/CT, ULS and other 3D mappings based on catheter 715. This input data 710 may include 3D mappings and imaging from several algorithms that analyze readings from the patient. This data 710 may include data per electrode/channel with the location in space (3 axial to 6 axial–X, Y, Z+Pitch, Roll, Yaw) over a period of time, intracardiac electrocardiogram over a period of time (for example 2500 milliseconds). This data 710 may include data per chamber including a 3D reconstruction, which may be in the form of a mesh, at least one imaging modality 735 (CT, MR, or set of Ultrasound fans). The patient data 725 may include demographic information, age, gender, weight, height, body mass index, ethnicity and other patient specific details including left atrial main axis lengths (width, height, length), left ventricular ejection fraction, hypertension, diabetes mellitus. Other baseline comorbidities may be included in the additional data 1010 including sleep apnea, coronary artery disease, valvular heart disease (e.g. mitral regurgitation), congestive heart disease. The patient medical history may be included in the patient data 725, and may include arrhythmia history, symptoms, and documented method, time since first diagnosis, anti-arrhythmia drug (AAD) history, previous cardiac ablations, anticoagulation, CHA2DS2-VASc Score, history of Thrombotic Diseases, New York Heart Association (NYHA) Grade of Cardiac Function, history of Hemorrhagic Diseases, HAS-BLED, respiration pattern, ventricular cycle length, atrial cycle length. Data per electrode/channel 715 and analyses performed on this data (e.g. derivatives, algorithmic calculations) may include local activation time, impedance over a period of time, impedance changes over time, rate of location changes (derivative of the position over time), maximal peak to peak voltage, unipolar and bi-polar measurements from far away regions (not the point or immediate surrounding), and the start and end time points of the time period in which the catheter was located at that point. Such time tagged data may provide insight because different points in the 3D mapping were calculated based on measurements done at different times. If a certain point value was triangulated by the algorithm rather than obtained from a visit of the catheter at that point, then a triangulation of relevant time points may be used. Data per chamber (can be epicardial map and/or endocardial map) may include wall motion from ULS, doppler from ULS, scar zones from MRI, chamber dimensions, Cycle Length Map, persistent Atrial Fibrillation Focal Sources Map (e.g. CARTOFINDER, or equivalent), persistent Atrial Fibrillation Rotational sources map (e.g. CARTOFINDER, or equivalent), reentrant/Fibrillation activation mapping (e.g. Coherent, or equivalent), ripple map, CFAE, ECG Fractionation, and 3D model of cardiac tissue, where each voxel has an indication of tissue elasticity at that voxel, based on data from Ultrasound readings.

The output 840 is a set of voxels representing cardiac tissue, where each voxel has two values including the level of scar and a confidence value associated with the level of scar. The level of scar may include a number from 0 to 1 with 1=most severe, no electricity passing, <1 & >0 borderline zone and 0=no scar. The confidence value may be provided between 0 and 1.

Between the input 710 and the output 840, the 3D mappings may be registered via a registration stage 820 as described above. The registered 3D mappings 735 may be input to the neural network 830 along with patient data and any additional data 1010 as described above. The neural network 830 may include an input layer 910, hidden layers, such as layers described as layers 920, 930, and output layer 940, each of which is described above with respect to FIGS. 8 and 9 to provide output 840.

Similar to the neural network of FIG. 10, the system 1100 of FIG. 11 utilizes a neural network in accordance with the embodiments described herein. System 1100 includes patient 725, additional data 1010, and 3D mappings 735, including, for example, MRI/CT, ULS and other 3D mappings based on catheter 715. This input data 710 is that which is input in to the other embodiments including system 1000.

Between the input 710 and the output 840, the 3D mappings may be registered via a registration stage 820 as described above. The registered 3D mappings 735 may be input to the neural network 830 along with patient data and any additional data 1010 as described above. The neural network 830 may include a first convolution and pooling 1110, followed by a second convolution and pooling 1120. The output from the convolutions and pooling 1110, 1120 may reshaped using reshaping 1150 and the reshaped data input to a dense layer 1130 and a dense output layer 1140 in series. Once the data is classified, the data reaches an output layer similar to output layer 940. The output layer provides the output 840.

The output 840, as described herein, is a set of voxels representing cardiac tissue, where each voxel has two values including the level of scar and a confidence value associated with the level of scar. The level of scar may include a number from 0 to 1 with 1=most severe, no electricity passing, <1 & >0 borderline zone and 0=no scar. The confidence value may be provided between 0 and 1.

In accordance with one or more embodiments, the technical effects and benefits of the system and method for identifying scar tissue include generation more accurate and higher resolution real-time image data for the ultrasound images without relying on a human operator's subjective interpretation (e.g., the generated real-time image data enables evaluations of the entire depth of the organic tissue, overcomes the lower resolution of conventional ultrasound imaging, and is relatively inexpensive and available compared to MRIs).

The flowchart and block diagrams in the figures illustrate the architecture, functionality, and operation of possible implementations of systems, methods, and computer program products according to various embodiments of the present invention. In this regard, each block in the flowchart or block diagrams may represent a module, segment, or portion of instructions, which includes one or more executable instructions for implementing the specified logical function(s). In some alternative implementations, the functions noted in the blocks may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Although features and elements are described above in particular combinations, one of ordinary skill in the art will appreciate that each feature or element can be used alone or in any combination with the other features and elements. In addition, the methods described herein may be implemented in a computer program, software, or firmware incorporated in a computer-readable medium for execution by a computer or processor. A computer readable medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire Examples of computer-readable media include electrical signals (transmitted over wired or wireless connections) and computer-readable storage media. Examples of computer-readable storage media include, but are not limited to, a register, cache memory, semiconductor memory devices, magnetic media such as internal hard disks and removable disks, magneto-optical media, optical media such as compact disks (CD) and digital versatile disks (DVDs), a random access memory (RAM), a read-only memory (ROM), an erasable programmable read-only memory (EPROM or Flash memory), a static random access memory (SRAM), and a memory stick. A processor in association with software may be used to implement a radio frequency transceiver for use in a terminal, base station, or any host computer.

The terminology used herein is for the purpose of describing particular embodiments only and is not intended to be limiting. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one more other features, integers, steps, operations, element components, and/or groups thereof.

The descriptions of the various embodiments herein have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method comprising:
   receiving, by a scar tissue identifier executed by a processor coupled to a memory, a first modality and a second modality, the first modality being of a first type, the second modality being of a second type that is different from the first type, each of the first modality and the second modality respectively describing organic tissue including at least one area of scar tissue of a patient according to the first and second types;
   cross referencing, by the scar tissue identifier, the first modality and the second modality, the cross referencing performed by the processor correlating corresponding locations of the first modality with locations of the second modality; and
   generating, by the scar tissue identifier, improved image data for the first modality based on the cross referencing, the improved image data comprising enhanced accuracy over or higher resolution than original data of the first modality by incorporating a benefit from an inclusion of data of the second modality.

2. The method of claim 1, wherein the scar tissue identifier generates a hybrid modality utilizing reciprocal improvements of the first modality and second modality.

3. The method of claim 1, wherein the scar tissue identifier is configured to utilize the improved image data to automatically identify scar areas within the organic tissue.

4. The method of claim 1, wherein the scar tissue identifier is configured to generate the improved image data by utilizing imaging processing to adjust and interpret the first modality based on the second modality.

5. The method of claim 1, wherein the first modality of the first type comprises an ultrasound image.

6. The method of claim 1, wherein the second modality of the second type comprises a late gadolinium enhancement—magnetic resonance imaging data.

7. The method of claim 1, wherein the scar tissue identifier utilizes the improved image data to implement machine learning for subsequent cross-referencing operations.

8. The method of claim 1, wherein cross referencing the first modality and the second modality comprises comparing the first modality to the second modality to match locations of the first modality to corresponding locations of the first modality.

9. The method of claim 1, wherein the scar tissue identifier receives and cross references a plurality of modalities of the first type with the second modality.

10. The method of claim 9, wherein the scar tissue identifier generates corresponding improved image data for each of the plurality of modalities based on the cross referencing.

11. The method of claim 1, wherein the scar tissue identifier is configured to receive a third modality of a third type that is different from the first and second types.

12. The method of claim 11, wherein the scar tissue identifier is configured to:
cross reference the first modality with the second modality and the third modality, and
generate the improved image data based on the cross referencing.

13. The method of claim 11, wherein the third modality of the third type comprises a cardiac map.

14. The method of claim 1, wherein the scar tissue identifier is incorporated into one or more of—ultrasound technologies, planning and diagnosis of lesions, ECG measurements, 3D mapping systems and assessment and diagnosis of magnetic resonance to address a disease state.

15. The method of claim 1, wherein a disease state comprises atrial fibrillation, atrial flutter, general electrophysiology, arrhythmias, ventricular fibrillation, or ventricular tachycardia.

16. A system comprising:
a memory storing processor executable instructions of a scar tissue identifier; and
a processor configured to execute the processor executable instructions of the scar tissue identifier to cause the system to:
receive a first modality and a second modality, the first modality being of a first type, the second modality being of a second type that is different from the first type, each of the first modality and the second modality respectively describing organic tissue including at least one area of scar tissue of a patient according to the first and second types;
cross reference the first modality and the second modality, the cross referencing iteratively correlating corresponding locations of the first modality with locations of the second modality; and
generate improved image data for the first modality based on the cross referencing, the improved image data comprising enhanced accuracy over or higher resolution than original data of the first modality by incorporating a benefit from an inclusion of data of the second modality.

17. The system of claim 16, wherein the scar tissue identifier generates a hybrid modality utilizing reciprocal improvements of the first modality and second modality.

18. The system of claim 16, wherein the scar tissue identifier is configured to utilize the improved image data to automatically identify scar areas within the organic tissue.

19. The system of claim 16, wherein the scar tissue identifier is configured to generate the improved image data by utilizing imaging processing to adjust and interpret the first modality based on the second modality.

20. The system of claim 16, wherein the first modality of the first type comprises an ultrasound image.

21. The system of claim 16, wherein the second modality of the second type comprises a late gadolinium enhancement—magnetic resonance imaging data.

22. The system of claim 16, wherein the scar tissue identifier utilizes the improved image data to implement machine learning for subsequent cross-referencing operations.

23. The system of claim 16, wherein cross referencing the first modality and the second modality comprises comparing the first modality to the second modality to match locations of the first modality to corresponding locations of the first modality.

24. The system of claim 16, wherein the scar tissue identifier receives and cross references a plurality of modalities of the first type with the second modality.

25. The system of claim 24, wherein the scar tissue identifier generates corresponding improved image data for each of the plurality of modalities based on the cross referencing.

26. The system of claim 16, wherein the scar tissue identifier is configured to receive a third modality of a third type that is different from the first and second types.

27. The system of claim 26, wherein the scar tissue identifier is configured to:
cross reference the first modality with the second modality and the third modality, and
generate the improved image data based on the cross referencing.

28. The system of claim 26, wherein the third modality of the third type comprises a cardiac map.

29. The system of claim 16, wherein the scar tissue identifier is incorporated into one or more of ultrasound technologies, planning and diagnosis of lesions, ECG and 3D Mapping and assessment and diagnosis of magnetic resonance to address a disease state.

30. The system of claim 16, wherein a disease state comprises atrial fibrillation, atrial flutter, general electrophysiology, arrhythmias, ventricular fibrillation, or ventricular tachycardia.

* * * * *

UNITED STATES PATENT AND TRADEMARK OFFICE
CERTIFICATE OF CORRECTION

| | |
|---|---|
| PATENT NO. | : 12,165,324 B2 |
| APPLICATION NO. | : 17/384989 |
| DATED | : December 10, 2024 |
| INVENTOR(S) | : Shmuel Auerbach et al. |

It is certified that error appears in the above-identified patent and that said Letters Patent is hereby corrected as shown below:

In the Specification

In Column 3, Line 32, delete "of an" and insert -- an --, therefor.

In Column 5, Line 6, delete "support of" and insert -- support --, therefor.

In Column 6, Line 4, delete "use" and insert -- used --, therefor.

In Column 8, Line 11, delete "the" and insert -- to the --, therefor.

In Column 10, Line 2, delete "and or" and insert -- and/or --, therefor.

In Column 15, Line 9, delete "the" and insert -- to the --, therefor.

In Column 15, Line 17, delete "a, smart phone," and insert -- a smartphone, --, therefor.

In Column 16, Line 15, delete "server a" and insert -- server in a --, therefor.

In Column 19, Line 56, delete "compared" and insert -- compared to --, therefor.

In Column 20, Line 53, delete "may to be" and insert -- to be --, therefor.

In Column 21, Line 29, delete "to training" and insert -- to train --, therefor.

In Column 23, Line 16, delete "(each" and insert -- each --, therefor.

In Column 23, Line 27, delete "may" and insert -- many --, therefor.

Signed and Sealed this
Fourth Day of February, 2025

Coke Morgan Stewart
*Acting Director of the United States Patent and Trademark Office*

In Column 25, Line 18, delete "more" and insert -- of more --, therefor.

In Column 25, Line 59, delete "wire" and insert -- wire. --, therefor.